(12) United States Patent
Simanzhenkov et al.

(10) Patent No.: US 12,168,219 B2
(45) Date of Patent: *Dec. 17, 2024

(54) MOLYBDENUM-VANADIUM-BERYLLIUM-BASED OXIDATIVE DEHYDROGENATION CATALYST MATERIALS

(71) Applicant: NOVA CHEMICALS (INTERNATIONAL) S.A., Fribourg (CH)

(72) Inventors: Vasily Simanzhenkov, Calgary (CA); Yoonhee Kim, Calgary (CA); David Sullivan, Calgary (CA); Marie Barnes, Calgary (CA); Elena Sebastiao, Calgary (CA)

(73) Assignee: NOVA Chemicals (International) S.A., Fribourg (CH)

(*) Notice: Subject to any disclaimer, the term of this patent is extended or adjusted under 35 U.S.C. 154(b) by 317 days.

This patent is subject to a terminal disclaimer.

(21) Appl. No.: 17/634,027

(22) PCT Filed: Aug. 28, 2020

(86) PCT No.: PCT/IB2020/058057
§ 371 (c)(1),
(2) Date: Feb. 9, 2022

(87) PCT Pub. No.: WO2021/044273
PCT Pub. Date: Mar. 11, 2021

(65) Prior Publication Data
US 2022/0288564 A1    Sep. 15, 2022

Related U.S. Application Data

(60) Provisional application No. 62/895,515, filed on Sep. 4, 2019.

(51) Int. Cl.
*B01J 23/28* (2006.01)
*B01J 21/04* (2006.01)
(Continued)

(52) U.S. Cl.
CPC ............... *B01J 23/28* (2013.01); *B01J 21/04* (2013.01); *B01J 35/393* (2024.01); *B01J 35/50* (2024.01);
(Continued)

(58) Field of Classification Search
CPC .......... B01J 21/04; B01J 23/28; B01J 35/393; C01G 39/006
See application file for complete search history.

(56) References Cited

U.S. PATENT DOCUMENTS

| 4,435,607 A * | 3/1984 | Imai ...................... C07C 5/3332 585/443 |
| 5,162,578 A | 11/1992 | McCain, Jr. et al. |

(Continued)

FOREIGN PATENT DOCUMENTS

| RU | 2668215 C1 * | 9/2018 |
| WO | WO 2020/016828 | 1/2020 |

OTHER PUBLICATIONS

Machine translation of RU2668215, publication date Sep. 27, 2018.*

(Continued)

*Primary Examiner* — Jun Li
(74) *Attorney, Agent, or Firm* — Fish & Richardson P.C.

(57) ABSTRACT

This document relates to oxidative dehydrogenation catalyst materials that include molybdenum, vanadium, beryllium, oxygen, and optionally aluminum.

16 Claims, 15 Drawing Sheets

(51) Int. Cl.
  *B01J 35/00* (2024.01)
  *B01J 35/02* (2006.01)
  *B01J 35/30* (2024.01)
  *B01J 35/50* (2024.01)
  *C01G 39/00* (2006.01)

(52) U.S. Cl.
  CPC ........ *C01G 39/006* (2013.01); *C01P 2002/02* (2013.01); *C01P 2002/50* (2013.01); *C01P 2002/60* (2013.01); *C01P 2002/72* (2013.01); *C01P 2002/82* (2013.01); *C01P 2004/03* (2013.01); *C01P 2004/61* (2013.01); *C01P 2004/62* (2013.01)

(56) References Cited

U.S. PATENT DOCUMENTS

| | | | | |
|---|---|---|---|---|
| 6,297,180 | B1* | 10/2001 | Maier | C07C 1/044 65/17.2 |
| 7,319,179 | B2* | 1/2008 | Lopez Nieto | B01J 37/10 502/328 |
| 10,130,936 | B2 | 11/2018 | Hossain et al. | |
| 11,230,512 | B2* | 1/2022 | Gao | B01J 37/06 |
| 11,338,274 | B2* | 5/2022 | Simanzhenkov | B01J 37/04 |
| 11,413,604 | B2* | 8/2022 | Simanzhenkov | B01J 35/30 |
| 2010/0256432 | A1* | 10/2010 | Arnold | C07C 5/48 585/655 |
| 2012/0016171 | A1* | 1/2012 | Kustov | B01J 37/0036 502/215 |
| 2019/0366311 | A1* | 12/2019 | Mestl | B01J 37/033 |
| 2020/0024215 | A1* | 1/2020 | Gao | B01J 27/0576 |
| 2020/0061583 | A1* | 2/2020 | Mestl | B01J 31/04 |
| 2020/0171475 | A1* | 6/2020 | Basset | B01J 29/42 |
| 2021/0354113 | A1* | 11/2021 | Park | B01J 23/34 |

OTHER PUBLICATIONS

International Preliminary Report on Patentability in International Appln. No. PCT/IB2020/058057, mailed on Nov. 2, 2010, 10 pages.
International Search Report and Written Opinion in International Appln. No. PCT/IB2020/058057, mailed on Nov. 6, 2020, 14 pages.
O'Connor et al., "Application of the Rietveld Refinement Procedure in Assaying Powdered Mixtures," Powder Diffraction, Mar. 1988, 3(1):2-6.

* cited by examiner

MOLYBDENUM-VANADIUM-BERYLLIUM-BASED OXIDATIVE DEHYDROGENATION CATALYST MATERIALS

CROSS-REFERENCE TO RELATED APPLICATION

This application is a National Stage Application under 35 U.S.C. § 371 and claims the benefit of International Application No. PCT/IB2020/058057, filed Aug. 28, 2020, which claims priority to U.S. Ser. No. 62/895,515, filed on Sep. 4, 2019. The disclosure of the prior applications is considered part of and is incorporated by reference in the disclosure of this application.

TECHNICAL FIELD

This document relates to oxidative dehydrogenation catalyst materials of alkanes such as ethane.

SUMMARY OF INVENTION

Provided in this disclosure is an oxidative dehydrogenation catalyst material that includes molybdenum, vanadium, beryllium, and oxygen. The molar ratio of molybdenum to vanadium is from 1:0.25 to 1:0.65. The molar ratio of molybdenum to beryllium is from 1:0.25 to 1:0.85. Oxygen is present at least in an amount to satisfy the valency of any present metal oxides.

In some embodiments, the molar ratio of molybdenum to vanadium is from 1:0.35 to 1:0.55. In some embodiments, the molar ratio of molybdenum to vanadium is from 1:0.38 to 1:0.48.

In some embodiments, the molar ratio of molybdenum to beryllium is from 1:0.35 to 1:0.75. In some embodiments, the molar ratio of molybdenum to beryllium is from 1:0.45 to 1:0.65.

In some embodiments, the catalyst material has a 35% conversion temperature from about 300° C. to about 400° C. In some embodiments, the catalyst material has a 35% conversion temperature from about 310° C. to about 375° C. In some embodiments, the catalyst material has a 35% conversion temperature from about 315° C. to about 345° C.

In some embodiments, the catalyst material has a selectivity to ethylene from about 65% to 99%. In some embodiments, the catalyst material has a selectivity to ethylene from about 75% to 97%. In some embodiments, the catalyst material has a selectivity to ethylene from about 85% to 95%.

In some embodiments, catalyst material has an amorphous phase of from 45 wt. % to 75 wt. %. In some embodiments, the catalyst material has an amorphous phase of from 55 wt. % to 65 wt. %.

In some embodiments, the catalyst material has an average crystallite size of greater than 50 nm. In some embodiments, the catalyst material has an average crystallite size of greater than 100 nm. In some embodiments, the catalyst material has an average crystallite size from 75 nm to 150 nm.

In some embodiments, the catalyst material has a mean particle size from 0.5 μm to 10 μm. In some embodiments, the catalyst material has a mean particle size from 2 μm to 8 μm. In some embodiments, the catalyst material has a mean particle size from 3 μm to 5 μm.

In some embodiments, the catalyst material is characterized by having at least one or more XRD diffraction peaks (2θ degrees) chosen from 6.5±0.2, 7.8±0.2, 8.9±0.2, 10.8±0.2, 13.2±0.2, 14.0±0.2, 22.1±0.2, 23.8±0.2, 25.2±0.2, 26.3±0.2, 26.6±0.2, 27.2±0.2, 27.6±0.2, 28.2±0.2, 29.2±0.2, 30.5±0.2, and 31.4±0.2 wherein the XRD is obtained using CuKα radiation.

Also provided in this disclosure is an oxidative dehydrogenation catalyst material that includes molybdenum, vanadium, beryllium, aluminum, and oxygen. The molar ratio of molybdenum to vanadium is from 1:0.25 to 1:0.65. The molar ratio of molybdenum to beryllium is from 1:0.25 to 1:1.7. The molar ratio of molybdenum to aluminum is from 1:1 to 1:9. Oxygen is present at least in an amount to satisfy the valency of any present metal oxides.

In some embodiments, the molar ratio of molybdenum to vanadium is from 1:0.35 to 1:0.55. In some embodiments, the molar ratio of molybdenum to vanadium is from 1:0.38 to 1:0.48.

In some embodiments, the molar ratio of molybdenum to beryllium is from 1:0.35 to 1:0.75. In some embodiments, the molar ratio of molybdenum to beryllium is from 1:0.45 to 1:0.65.

In some embodiments, the molar ratio of molybdenum to aluminum is from 1:2 to 1:8. In some embodiments, the molar ratio of molybdenum to aluminum is from 1:4 to 1:6.

In some embodiments, at least a portion of the aluminum in the catalyst material is present as an aluminum oxide. In some embodiments, the aluminum oxide includes an aluminum oxide hydroxide. In some embodiments, the aluminum oxide hydroxide includes an aluminum oxide hydroxide selected from a gibbsite, a bayerite, a boehmite, or a combination thereof. In some embodiments, the aluminum oxide hydroxide includes a boehmite.

In some embodiments, at least a portion of the aluminum in the catalyst material is present as gamma alumina.

In some embodiments, the catalyst material has a 35% conversion temperature from about 300° C. to about 400° C. In some embodiments, the catalyst material has a 35% conversion temperature from about 310° C. to about 375° C. In some embodiments, the catalyst material has a 35% conversion temperature from about 315° C. to about 345° C.

In some embodiments, the catalyst material has a selectivity to ethylene from about 65% to 99%. In some embodiments, the catalyst material has a selectivity to ethylene from about 75% to 97%. In some embodiments, the catalyst material has a selectivity to ethylene from about 85% to 95%.

In some embodiments, the catalyst material has an amorphous phase of from 50 wt. % to 80 wt. %. In some embodiments, the catalyst material has an amorphous phase of from 55 wt. % to 75 wt. %. In some embodiments, the catalyst material has an amorphous phase of from 60 wt. % to 70 wt. %.

In some embodiments, the catalyst material has an average crystallite size of greater than 75 nm. In some embodiments, the catalyst material has an average crystallite size of greater than 125 nm. In some embodiments, the catalyst material has an average crystallite size from 75 nm to 250 nm. In some embodiments, the catalyst material has an average crystallite size from 125 nm to 175 nm.

In some embodiments, the catalyst material has a mean particle size from 0.5 μm to 20 μm. In some embodiments, the catalyst material has a mean particle size from 5 μm to 15 μm. In some embodiments, the catalyst material has a mean particle size from 7 μm to 11 μm.

In some embodiments, the catalyst material is characterized by having at least one or more XRD diffraction peaks (2θ degrees) chosen from 6.6±0.2, 6.8±0.2, 8.9±0.2, 10.8±0.2, 13.0±0.2, 22.1±0.2, 26.7±0.2, 27.2±0.2, and 28.2±0.2, wherein the XRD is obtained using CuKα radiation.

In some embodiments, the catalyst material has a crush strength from 0.66 N/mm to 200 N/mm. In some embodiments, the catalyst material has a crush strength from 2 N/mm to 4 N/mm.

In some embodiments, the catalyst material has a bulk density from 0.1 g/mL to 2 g/mL. In some embodiments, the catalyst material has a bulk density from 0.3 g/mL to 0.7 g/mL.

In some embodiments, the catalyst material includes from about 0.8 wt. % to about 30 wt. % calcium. In some embodiments, the catalyst material includes about 0.15 wt. % to about 2.8 wt. % calcium.

In some embodiments, the catalyst material includes 0.5 wt. % to 75 wt. % calcium carbonate. In some embodiments, the catalyst material includes 5 wt. % to 15 wt. % calcium carbonate.

DESCRIPTION OF EMBODIMENTS

Figure 1:
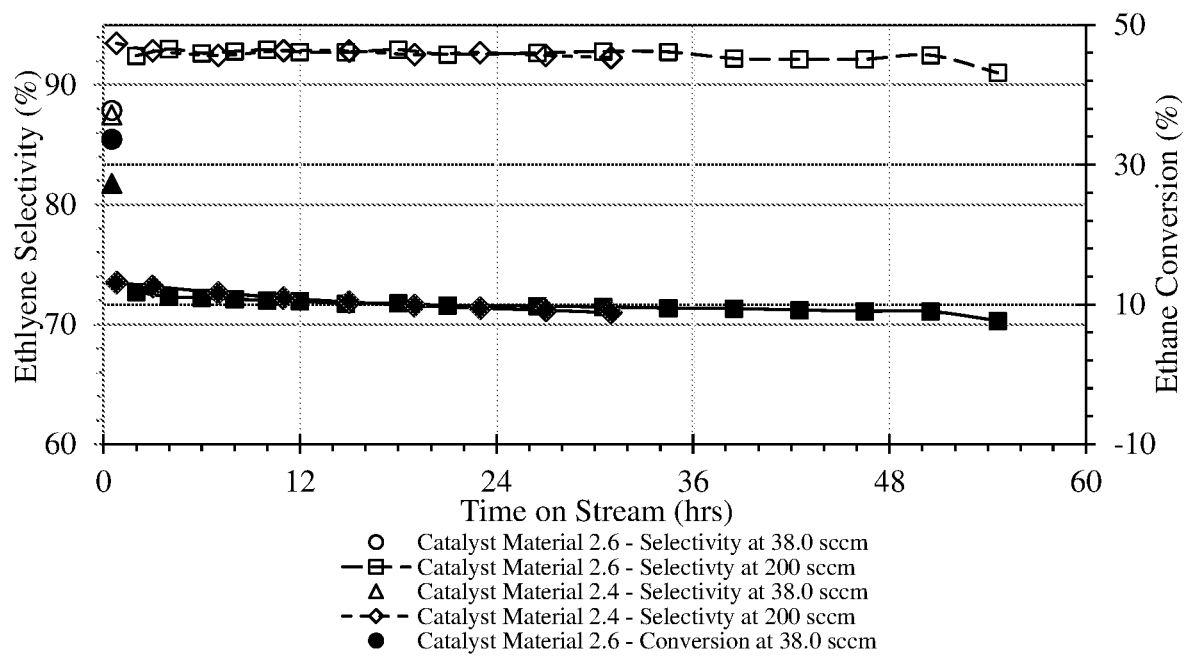
FIG. 1 shows overlaid MRU raw data for Catalyst Material 2.4 and Catalyst Material 2.6.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

Provided in this disclosure is an oxidative dehydrogenation catalyst material that includes molybdenum, vanadium, beryllium, and oxygen. The molar ratio of molybdenum to vanadium is from 1:0.25 to 1:0.65. The molar ratio of molybdenum to beryllium is from 1:0.25 to 1:85. Further, oxygen is present at least in an amount to satisfy the valency of any present metal oxides.

As used herein, the term "catalyst material" refers to a material that can promote the oxidative dehydrogenation of ethane to ethylene. The catalyst material can be a plurality of particles or a formed catalyst material. Non-limiting examples of formed catalyst materials include extruded catalyst materials, pressed catalyst materials, and cast catalyst materials. Non-limiting examples of pressed and cast catalyst materials includes pellets-such as tablets, ovals, and spherical particles.

Unless stated otherwise, the molar ratio of molybdenum, vanadium, iron, aluminum, and optionally other elements in the catalysts and catalyst materials described herein is determined by employing inductively coupled plasma mass spectrometry ICP-MS.

In some embodiments, the molar ratio of molybdenum to vanadium is from 1:0.35 to 1:0.55. For example, the molar ratio of molybdenum to vanadium can be from 1:0.38 to 1:0.48.

In some embodiments, the molar ratio of molybdenum to beryllium is from 1:0.35 to 1:0.75. For example, the molar ratio of molybdenum to beryllium can be from 1:0.45 to 1:0.65.

In some embodiments, the catalyst material does not include niobium, tellurium, or both.

The catalyst material can have a 35% conversion temperature from about 300° C. to about 400° C. For example, the catalyst material can have a 35% conversion temperature from about 310° C. to about 375° C. In some embodiments, the catalyst material has a 35% conversion temperature from about 315° C. to about 345° C.

As used in this disclosure, the phrase "35% conversion temperature" refers to the temperature at which 35% of ethane in a gas stream is converted to a product other than ethane. The 35% conversion temperature of an oxidative dehydrogenation catalyst or catalyst material can be determined by using a microreactor unit (MRU). In a microreactor unit, the 35% conversion temperature of a catalyst or catalyst material can be determined by passing a feed gas over a catalyst bed in a reactor tube. The MRU reactor tube has an outer diameter of about 0.5 inches and an internal diameter of about 0.4 inches and length of about 15 inches. For example, the reactor tube can be stainless-steel SWAGELOK® Tubing with a wall thickness of about 0.049 inches. The feed gas can include ethane and oxygen having a molar ratio of 70:30 to 90:10. For example, the feed gas can include ethane and oxygen having a molar ratio of 82:18. Alternatively, the feed gas can include ethane, oxygen, and nitrogen. The molar ratio of ethane to oxygen to nitrogen can be 18:18:64 to 54:18:28. For example, the molar ratio of ethane to oxygen to nitrogen can be 36:18:46 or 35:17.5:47.5. The flow rate of the feed gas can be about 70 standard cubic centimeters per minute (sccm) to about 80 sccm. For example, the flow rate of the feed gas can be about 76 sccm (e.g., 76.1 sccm). The catalyst bed consists of the oxidative dehydrogenation catalyst and a filler, such as sand, in a one to one volume ratio, with the total weight for the oxidative dehydrogenation catalyst being 2.00 g. Any remaining space in the reactor tube (e.g., below or above the catalyst bed) is packed with an additional filler, such as quartz sand. The 35% conversion temperature is determined at a weight hourly space velocity (WHSV) of 2.90 h$^{-1}$, with the WHSV based on the active phase, and a gas hourly space velocity (GHSV) of about 2,000 to 3,000 h$^{-1}$. Typically, the inlet pressure is in the range of about 1 pound per square inch gauge (psig) to about 2.5 psig and the outlet pressure is in the range of about 0 psig to about 0.5 psig. The gas feed exiting the catalyst bed is analyzed by gas chromatography to determine the percent of various hydrocarbons (e.g., ethane and ethylene) and, optionally other gases such as $O_2$, $CO_2$, and CO. Conversion of the feed gas is calculated as a mass flow rate change of ethane in the product compared to feed ethane mass flow rate using the following formula:

$$C = \left( \frac{2X_{Ethylene} + X_{CO_2} + X_{CO}}{2X_{Ethylene} + 2X_{Ethane} + X_{CO_2} + X_{CO}} \right) * 100$$

wherein C is the percent (molar percent) of feed gas that has been converted from ethane to another product (i.e., ethane conversion) and X is the molar concentration of the corresponding compound in the gaseous effluent exiting the reactor. The ethane conversion is then plotted as a function of temperatures to acquire a linear algebraic equation. The linear equation for ethane conversion is solved to determine the temperature in which the ethane conversion is 35% (i.e. the 35% conversion temperature). Not taken into account for calculating the 35% conversion of ethane temperature or selectivity to ethylene, were reaction the products exiting the reactor in an aqueous stream such as, but not limited to, acetic acid, maleic acid, propionic acid, ethanol, and acetaldehyde.

In some embodiments, the catalyst material has a selectivity to ethylene from about 65% to 99%. For example, the catalyst material can have a selectivity to ethylene from about 75% to 97%. In some embodiments, the catalyst material has a selectivity to ethylene from about 85% to 95%.

As used in this disclosure, the phrase "selectivity to ethylene" refers to the percentage on a molar basis of converted or reacted ethane that forms ethylene. An oxidative dehydrogenation catalyst's selectivity to ethylene can be determined using an MRU as discussed above. An oxidative dehydrogenation catalyst's selectivity to ethylene can be determined using to the following equation:

$$S_{Ethylene} = \left( \frac{2 * X_{Ethylene}}{2 * X_{Ethylene} + X_{CO2} + X_{CO}} \right) * 100\%$$

wherein $S_{Ethylene}$ is the selectivity to ethylene, and X is the molar concentration of the corresponding compound in the gaseous effluent exiting the reactor. Notably, the selectivity to ethylene is determined at the 35% conversion temperature, unless otherwise indicated. As such, after the 35% conversion temperature is determined, the above equation for selectivity is solved using the corresponding values for $X_{Ethylene}$, $X_{CO2}$, and $X_{CO}$ at the 35% conversion temperature.

In some embodiments, the catalyst material has an amorphous phase of from 45 wt. % to 75 wt. % or from 50 wt. % to 70 wt. %. In some embodiments, the catalyst material can have an amorphous phase of from 55 wt. % to 65 wt. %.

The weight percent of amorphous phase of a catalyst material can be determined as described in the examples section of this disclosure.

In some embodiments, the catalyst material has an average crystallite size of greater than 50 nm. For example, the catalyst material can have an average crystallite size of greater than 100 nm. In some embodiments, the catalyst material has an average crystallite size from 75 nm to 150 nm. For example, the catalyst material can have a mean particle size from 0.5 µm to 10 µm.

The average crystallite size of catalyst material can be determined as described in the examples section of this disclosure.

In some embodiments, the catalyst material has a mean particle size from 2 µm to 8 µm. For example, the catalyst material can have a mean particle size from 3 µm to 5 µm.

The mean particle size of catalyst material can be determined as described in the examples section of this disclosure.

In some embodiments, the catalyst material is characterized by having at least one or more XRD diffraction peaks (2θ degrees) chosen from 6.5±0.2, 7.8±0.2, 8.9±0.2, 10.8±0.2, 13.2±0.2, 14.0±0.2, 22.1±0.2, 23.8±0.2, 25.3±0.2, 26.3±0.2, 26.6±0.2, 27.2±0.2, 27.6±0.2, 28.2±0.2, 29.2±0.2, 30.5±0.2, 31.4±0.2 wherein the XRD is obtained using CuKα radiation.

In some embodiments, the catalyst material is characterized by having at least five XRD diffraction peaks (2θ degrees) chosen from 6.6±0.2, 7.8±0.2, 9.0±0.2, 10.8±0.2, 22.1±0.2, 26.3±0.2, 26.7±0.2, 27.2±0.2, 28.2±0.2, 29.3±0.2, 30.5±0.2, 31.4±0.2, 31.9±0.2, 41.2±0.2, 43.8±0.2, 45.2±0.2, 51.3±0.2, 51.9±0.2, and 55.5±0.2, wherein the XRD is obtained using CuKα radiation.

In some embodiments, the catalyst material is characterized by having at least ten XRD diffraction peaks (2θ degrees) chosen from 6.6±0.2, 7.8±0.2, 9.0±0.2, 10.8±0.2, 22.1±0.2, 26.3±0.2, 26.7±0.2, 27.2±0.2, 28.2±0.2, 29.3±0.2, 30.5±0.2, 31.4±0.2, 31.9±0.2, 41.2±0.2, 43.8±0.2, 45.2±0.2, 51.3±0.2, 51.9±0.2, and 55.5±0.2, wherein the XRD is obtained using CuKα radiation.

In some embodiments, the catalyst material is characterized by having at least fifteen XRD diffraction peaks (2θ degrees) chosen from 6.6±0.2, 7.8±0.2, 9.0±0.2, 10.8±0.2, 22.1±0.2, 26.3±0.2, 26.7±0.2, 27.2±0.2, 28.2±0.2, 29.3±0.2, 30.5±0.2, 31.4±0.2, 31.9±0.2, 41.2±0.2, 43.8±0.2, 45.2±0.2, 51.3±0.2, 51.9±0.2, and 55.5±0.2, wherein the XRD is obtained using CuKα radiation.

In some embodiments, the catalyst material is characterized by having XRD diffraction peaks (2θ degrees) at 6.6±0.2, 7.8±0.2, 9.0±0.2, 10.8±0.2, 22.1±0.2, 26.3±0.2, 26.7±0.2, 27.2±0.2, 28.2±0.2, 29.3±0.2, 30.5±0.2, 31.4±0.2, 31.9±0.2, 41.2±0.2, 43.8±0.2, 45.2±0.2, 51.3±0.2, 51.9±0.2, and 55.5±0.2, wherein the XRD is obtained using CuKα radiation.

Further provided in this disclosure is an oxidative dehydrogenation catalyst material that includes molybdenum, vanadium, beryllium, aluminum, and oxygen. The molar ratio of molybdenum to vanadium is from 1:0.25 to 1:0.65. The molar ratio of molybdenum to beryllium is from 1:0.25 to 1:7. The molar ratio of molybdenum to aluminum is from 1:1 to 1:9. Further, oxygen is present at least in an amount to satisfy the valency of any present metal oxides.

In some embodiments, the molar ratio of molybdenum to vanadium is from 1:0.25 to 1:0.85 or from 1:0.35 to 1:0.55. For example, the molar ratio of molybdenum to vanadium can be from 1:0.38 to 1:0.48.

In some embodiments, the molar ratio of molybdenum to beryllium is from 1:0.35 to 1:0.75. For example, the molar ratio of molybdenum to beryllium can be from 1:0.45 to 1:0.65.

In some embodiments, the molar ratio of molybdenum to aluminum is from 1:2 to 1:8. For example, the molar ratio of molybdenum to aluminum can be from 1:4 to 1:6.

In some embodiments, at least a portion of the aluminum in the catalyst material is present as an aluminum oxide. In some embodiments, the aluminum oxide is an aluminum oxide hydroxide. In some embodiments, the aluminum oxide hydroxide includes an aluminum oxide hydroxide selected from a gibbsite, a bayerite, a boehmite, or a combination thereof. In some embodiments, the aluminum oxide hydroxide includes a boehmite. In some embodiments, the boehmite includes a pseudoboehmite such as VERSAL™ 250. VERSAL™ 250 has a dispersibility index (%<1 mu) of 20-30, a bulk density of 12-16 pounds per cubic foot (lbs/ft³), a surface area of about 320 meters squared per gram (m²/g), and a loss on ignition (LOI) of about 26 wt. %. The dispersibility index for VERSAL™ 250 can be determined by using 8 grams of sample on a volatile free basis and 96 milliliters (mL) of 0.22 normal (N) nitric acid solution, which is approximately 260 meq nitric acid per 100 grams (g) of alumina, mixing the acidic alumina slurry in a WARING® blender at low speed (17000 rpm) for 5 min, and then determining particle size distribution by using a SEDIGRAPH® PSA—with the results reported as wt. % submicron particles. In some embodiments, the boehmite includes CATAPAL® B. CATAPAL® B is an alumina hydrate that has a loose bulk density of 670 to 750 g/L, a packed bulk density of 800 to 1100 g/L, a particle size ($d_{50}$) of 60 μm, a surface area (BET) after activation at 550° C. for 3 hours of 250 m²/g, a pore volume after activation at 550° C. for 3 hours of 0.5 mL/g, and a crystallite size (120) of about 4.5 nm.

In some embodiments, at least a portion of the aluminum in the catalyst material is present as gamma alumina.

In some embodiments, the catalyst material does not include niobium, tellurium, or both.

In some embodiments, the catalyst material has a 35% conversion temperature from about 300° C. to about 400° C. For example, the catalyst material can have a 35% conversion temperature from about 310° C. to about 375° C. In some embodiments, the catalyst material has a 35% conversion temperature from about 315° C. to about 345° C.

In some embodiments, the catalyst material has a selectivity to ethylene from about 65% to 99%. For example, the catalyst material can have a selectivity to ethylene from about 75% to 97%. In some embodiments, the catalyst material has a selectivity to ethylene from about 85% to 95%.

In some embodiments, the catalyst material has an amorphous phase from 50 wt. % to 80 wt. %. For example, the catalyst material can have an amorphous phase from 55 wt. % to 75 wt. %. In some embodiments, the catalyst material has an amorphous phase from 60 wt. % to 70 wt. %.

In some embodiments, the catalyst material has an average crystallite size of greater than 75 nm. For example, the catalyst material can have an average crystallite size of greater than 125 nm. In some embodiments, the catalyst material has an average crystallite size from 75 nm to 250 nm. For example, the catalyst material can have an average crystallite size from 125 nm to 175 nm.

In some embodiments, the catalyst material has a mean particle size from 0.5 μm to 20 μm. For example, the catalyst material can have a mean particle size from 5 μm to 15 μm. In some embodiments, the catalyst material has a mean particle size from 7 μm to 11 μm.

In some embodiments, the catalyst material is characterized by having at least one or more XRD diffraction peaks (2θ degrees) chosen from 6.6±0.2, 6.8±0.2, 8.9±0.2, 10.8±0.2, 13.0±0.2, 22.1±0.2, 26.7±0.2, 27.2±0.2, and 28.2±0.2, wherein the XRD is obtained using CuKα radiation.

In some embodiments, the catalyst material is characterized by having at least five XRD diffraction peaks (2θ degrees) chosen from 6.6±0.2, 7.8±0.2, 9.0±0.2, 10.8±0.2, 22.1±0.2, 26.3±0.2, 26.7±0.2, 27.2±0.2, 28.2±0.2, 29.3±0.2, 30.5±0.2, 31.4±0.2, 31.9±0.2, 41.2±0.2, 43.8±0.2, 45.2±0.2, 51.3±0.2, 51.9±0.2, and 55.5±0.2, wherein the XRD is obtained using CuKα radiation.

In some embodiments, the catalyst material is characterized by having at least ten XRD diffraction peaks (2θ degrees) chosen from 6.6±0.2, 7.8±0.2, 9.0±0.2, 10.8±0.2, 22.1±0.2, 26.3±0.2, 26.7±0.2, 27.2±0.2, 28.2±0.2, 29.3±0.2, 30.5±0.2, 31.4±0.2, 31.9±0.2, 41.2±0.2, 43.8±0.2, 45.2±0.2, 51.3±0.2, 51.9±0.2, and 55.5±0.2, wherein the XRD is obtained using CuKα radiation.

In some embodiments, the catalyst material is characterized by having at least fifteen XRD diffraction peaks (2θ degrees) chosen from 6.6±0.2, 7.8±0.2, 9.0±0.2, 10.8±0.2, 22.1±0.2, 26.3±0.2, 26.7±0.2, 27.2±0.2, 28.2±0.2, 29.3±0.2, 30.5±0.2, 31.4±0.2, 31.9±0.2, 41.2±0.2, 43.8±0.2, 45.2±0.2, 51.3±0.2, 51.9±0.2, and 55.5±0.2, wherein the XRD is obtained using CuKα radiation.

In some embodiments, the catalyst material is characterized by having XRD diffraction peaks (2θ degrees) at 6.6±0.2, 7.8±0.2, 9.0±0.2, 10.8±0.2, 22.1±0.2, 26.3±0.2, 26.7±0.2, 27.2±0.2, 28.2±0.2, 29.3±0.2, 30.5±0.2, 31.4±0.2, 31.9±0.2, 41.2±0.2, 43.8±0.2, 45.2±0.2, 51.3±0.2, 51.9±0.2, and 55.5±0.2, wherein the XRD is obtained using CuKα radiation.

In some embodiments, the catalyst material has a longitudinal crush strength from 0.66 N/mm to 200 N/mm, from 0.66 N/mm to 150 N/mm, from 0.66 N/mm to 100 N/mm, from 0.66 N/mm to 50 N/mm, 0.66 N/mm to 6.67 N/mm. For example, the catalyst material can have a longitudinal crush strength from 0.2 N/mm to 4 N/mm.

In some embodiments, the catalyst material has a bulk density from 0.1 g/mL to 2 g/mL. For example, the catalyst material can have a bulk density from 0.3 g/mL to 0.7 g/mL.

In some embodiments, the catalyst material further includes calcium. For example, the catalyst material can include from about 0.8 wt. % to about 30 wt. %, about 0.8 wt. % to about 20 wt. %, about 0.8 wt. % to about 10 wt. %, or from about 2 wt. % to about 6 wt. % calcium. In some embodiments, the catalyst material includes from about 0.15 wt. % to about 2.8 wt. % calcium. In some embodiments, the catalyst material includes from about 5 wt. % to about 10 wt. % calcium, about 10 wt. % to about 15 wt. %, about 15 wt. % to about 20 wt. %, about 20 wt. % to about 25 wt. %, or from about 25 wt. % to about 30 wt. % calcium.

In some embodiments, the catalyst material further includes calcium carbonate. For example, the catalyst material can include from about 2 wt. % to about 75 wt. %, about 2 wt. % to about 50 wt. %, about 2 wt. % to about 25 wt. %, or about 5 wt. % to about 15 wt. % calcium carbonate. In some embodiments, the catalyst material includes about 0.5 wt. % to about 7 wt. % calcium carbonate. In some embodiments, the catalyst material includes about 15 wt. % to about 25 wt. %, about 25 wt. % to about 35 wt. %, about 35 wt. % to about 45 wt. %, about 45 wt. % to about 55 wt. %, about 55 wt. % to about 65 wt. %, or about 65 wt. % to about 75 wt. % calcium carbonate.

Also provided herein is a method for the oxidative dehydrogenation of ethane to ethylene in an oxidative dehydrogenation reactor with any of the oxidative dehydrogenation catalyst materials described herein.

Ethylene can subsequently be converted into a variety of products. For example, ethylene can be converted into many various compounds including low density polyethylene, high density polyethylene, ethylene dichloride, ethylene oxide, ethylbenzene, linear alcohols, vinyl acetate, alkanes, alpha olefins (e.g., 1-hexene and 1-octeene), various hydrocarbon-based fuels, ethanol and the like. These compounds can then be further processed using methods well known to one of ordinary skill in the art to obtain other valuable chemicals and consumer products.

EXAMPLES

Experimental Methods
Reagents

Reagents purchased from manufacturers were used as received, without further purification and their purities were reported by the manufacturers. All reagents, with the exception of alumina, were purchased from Sigma Aldrich. These included Beryllium oxide (BeO), ammonium molybdate ($(NH_4)_6Mo_7O_{24}.4H_2O$), vanadium (IV) oxide sulfate hydrate ($VOSO_4 \cdot 3.46H_2O$ and $VOSO_4 \cdot 3.36H_2O$), and sodium dodecyl sulfate (SDS). The supplied certificates of analysis were used to establish the hydrate content for different batches of ammonium molybdate and vanadium (IV) oxide sulfate hydrate. Beryllium oxide had a purity of 99.98% according to trace metals basis. The purity of sodium dodecyl sulfate was ≥99.0%, as determined by titration based on the total alkyl sulfate content in the sample.

Versal Alumina V-250 was manufactured from UOP.

Distilled water was prepared inhouse using a Corning Mega Pure 12A System ACS as distillation apparatus.

Catalyst Material Mixing Methods
Wet Mixing—Slow Evaporation Method

Components are mixed with an overhead agitator in an amount of water sufficient to form a thick slurry. As the components are mixed with the overhead agitator, the water was evaporated in an oil bath until a thick paste was formed. The paste was placed in an oven at 90° C. to evaporate excess water.

Wet Mixing—Paste Method

Components are mixed manually with a minimum amount of water to form a thick paste. The paste was placed in an oven at 90° C. to evaporate excess water.

Dry Mixing—Dry Mixing Method

Components are mixed dry, with no use of water.

Pressing Equipment

A CPR-6 automatic single punch tablet press from DOTT BONAPACE&C, which has the capability of an adjustable force up to 2.5 metric tons, was used to press the catalyst materials with different additives into 0.125" OD cylindrical shape. This press was used on Catalyst Material 1.1, 1.2, 2.2, 2.2.1, and 2.3.1.

RTP41 automated rotary tablet press was used to press Catalyst Material 4.1.1 (pressing was outsourced to FeMo Cat Ltd.). The RTP41's 4 Kw motor produces a maximum of 80 kN of pressure and powers 41 sets of dies. The maximum production capacity was approximately 180,000 pellets an hour, depending on the materials being pressed and set rpm of the die wheel. The maximum diameter of each tablet was 12 mm and the maximum thickness is 6 mm, with a depth of fill up to 15 mm. The turret speed ranged from 14-37 rpm.

Microreactor Unit

The ability of catalysts and catalyst materials described herein to participate in the oxidative dehydrogenation of ethane was tested in a microreactor unit (MRU).

Setup A

The MRU included a reactor tube made from SS316L stainless-steel SWAGELOK® Tubing, which had an outer diameter of 0.5 inches, an internal diameter of about 0.4 inches, and a length of about 15 inches. A 6-point WIKA Instruments Ltd. K-type thermocouple having an outer diameter of 0.125 inches was inserted axially through the center of the reactor, which was used to measure and control the temperature within the catalyst bed. A room temperature glass tight sealed condenser was located after the reactor to collect water/acidic acid condensates. The gas product flow was allowed to either vent or was directed to a gas chromatography (Agilent 6890N Gas Chromatograph, using CHROMPERFECT®—Analysis, Version 6.1.10 for data evaluation) via a sampling loop.

For the MRU testing, a pre-mixed feed gas was fed through the reactor. The pre-mixed feed gas entering the reactor was 36 mol. % ethane, 18 mol. % oxygen, and 46 mol. % nitrogen. Further, the pre-mixed feed gas flow was adjusted by a calibrated mass flow controller to obtain a gas hourly space velocity (GHSV) of about 3,000 $h^{-1}$, based on the catalyst volume in the catalyst bed.

The flow rate of the feed gas was between about 70 standard cubic centimeters per minute (sccm) to about 80 sccm (e.g., 76.1 sccm). The catalyst bed placed in the reactor tube can include the catalyst or catalyst material and a filler.

With reference to the MRU's catalyst bed, a filler refers to a material that does not participate in the oxidative dehydrogenation of ethane or have other catalytic activity, such as non-selective oxidation under the MRU test conditions. The filler was quartz sand. The 35% conversion temperature was determined at a weight hourly space velocity (WHSV) of 2.90 h$^{-1}$, with the WHSV based on the amount of catalyst or the amount of catalyst used to prepare the catalyst material, and a gas hourly space velocity (GHSV) of about 3,000 h$^{-1}$. Whereby WHSV was defined as mass flow of feed gas to the reactor divided by the weight of the catalyst in the catalyst bed, GHSV was defined as volumetric flow of the reactor feed gas divided by the volume of the catalyst bed.

Typically, the inlet pressure was in the range of about 1 pound per square inch gauge (psig) to about 2.5 psig and the outlet pressure was in the range of about 0 psig to about 0.5 psig. The gas feed exiting the catalyst bed was be analyzed by gas chromatography to determine the percent of various hydrocarbons (e.g., ethane and ethylene) and, optionally other gases such as $O_2$, $CO_2$, and CO.

Setup A was employed for all samples except Catalyst Material 4.1.1.

Setup B

The MRU included a reactor tube made from SS316L stainless-steel SWAGELOK® Tubing, which had an outer diameter of 0.5 inches, an internal diameter of about 0.4 inches, and a length of about 15 inches. A 6-point WIKA Instruments Ltd. K-type thermocouple having an outer diameter of 0.125 inches was inserted axially through the center of the reactor, which was used to measure and control the temperature within the catalyst bed. A room temperature 316 SS sealed condenser was located after the reactor to collect water/acidic acid condensates. The gas product flow was allowed to either vent or was directed to a gas chromatography (Agilent 6890N Gas Chromatograph, using CHROMPERFECT®—Analysis, Version 6.1.10 for data evaluation) via a sampling loop.

For the MRU testing, a pre-mixed feed gas was fed through the reactor. The pre-mixed feed gas entering the reactor was 36 mol. % ethane, 18 mol. % oxygen, and 46 mol. % nitrogen. Further, the pre-mixed feed gas flow was adjusted by a calibrated mass flow controller to obtain a gas hourly space velocity (GHSV) of about 5,619 h$^{-1}$, based on the catalyst volume in the catalyst bed.

The flow rate of the feed gas was about 150 sccm. The catalyst bed placed in the reactor tube can include the catalyst or catalyst material and a filler. With reference to the MRU's catalyst bed, a filler refers to a material that does not participate in the oxidative dehydrogenation of ethane or have other catalytic activity, such as non-selective oxidation under the MRU test conditions. The filler was quartz sand. The 35% conversion temperature was determined at a weight hourly space velocity (WHSV) of 9.16 h$^{-1}$, with the WHSV based on the amount of catalyst or the amount of catalyst used to prepare the catalyst material, and a gas hourly space velocity (GHSV) of about 5,619 h$^{-1}$. Whereby WHSV was defined as mass flow of feed gas to the reactor divided by the weight of the catalyst in the catalyst bed, GHSV was defined as volumetric flow of the reactor feed gas divided by the volume of the catalyst bed.

Typically, the inlet pressure was in the range of about 1 pound per square inch gauge (psig) to about 2.5 psig and the outlet pressure was in the range of about 0 psig to about 0.5 psig. The gas feed exiting the catalyst bed was be analyzed by gas chromatography to determine the percent of various hydrocarbons (e.g., ethane and ethylene) and, optionally other gases such as $O_2$, $CO_2$, and CO.

Setup B was employed for Catalyst Material 4.1 and Catalyst Material 4.1.1.

Common to Both Setup a and Setup B

To prepare catalyst and catalyst materials for testing in the MRU, the catalyst or catalyst material was loaded into a 1-inch round die and pressed with 8 tons of compression force for 10 to 15 seconds of dwelling time. The pressed catalyst or catalyst material was then crushed into small pieces using a mortar and pestle. Note: for catalyst materials which were pressed on the CPR-6 Automated press, the 3×3 mm pellets were gently crushed with a mortar and pestle. The crushed catalyst or catalyst material was then sieved and a particle sizes between 425 µm and 1 mm were collected to be loaded for testing on the MRU.

Figure 9:
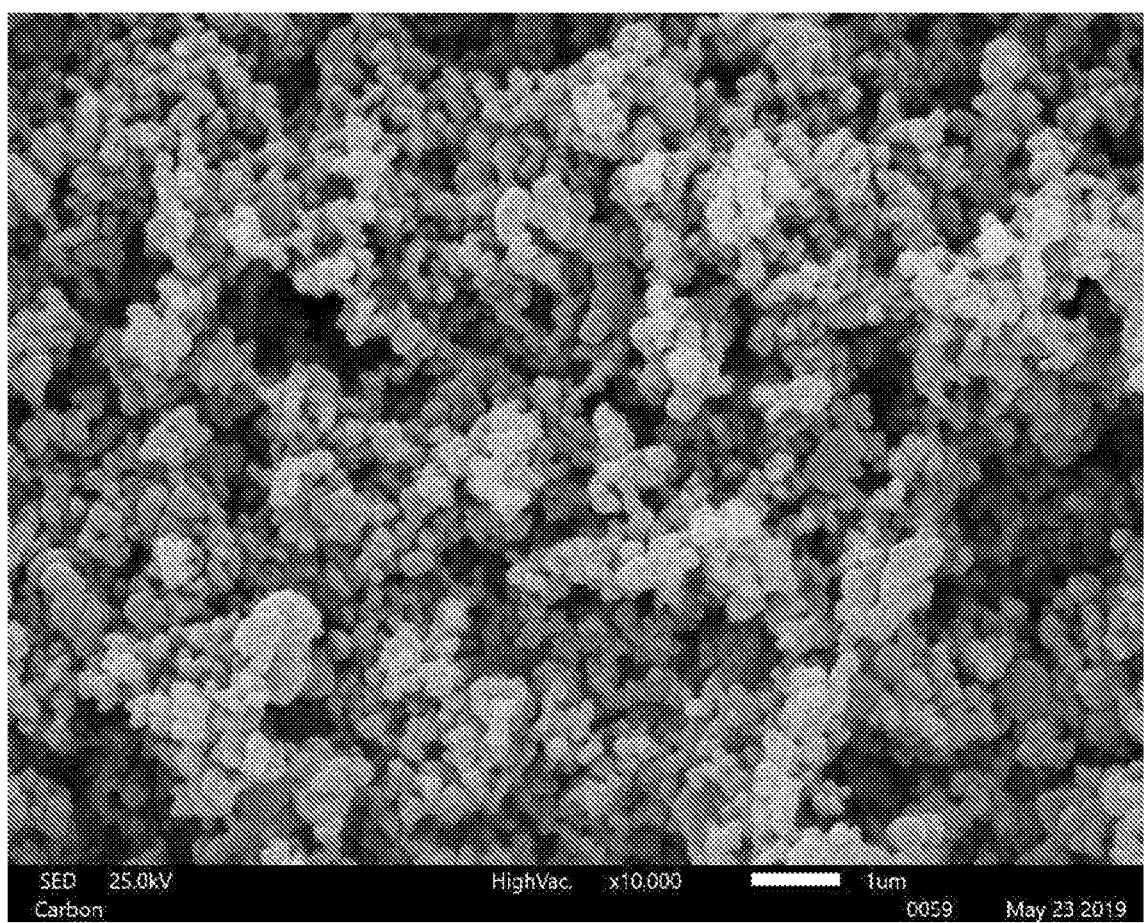
FIG. 9 shows a 10,000× magnification SEM image of BeO.
Figure 10:
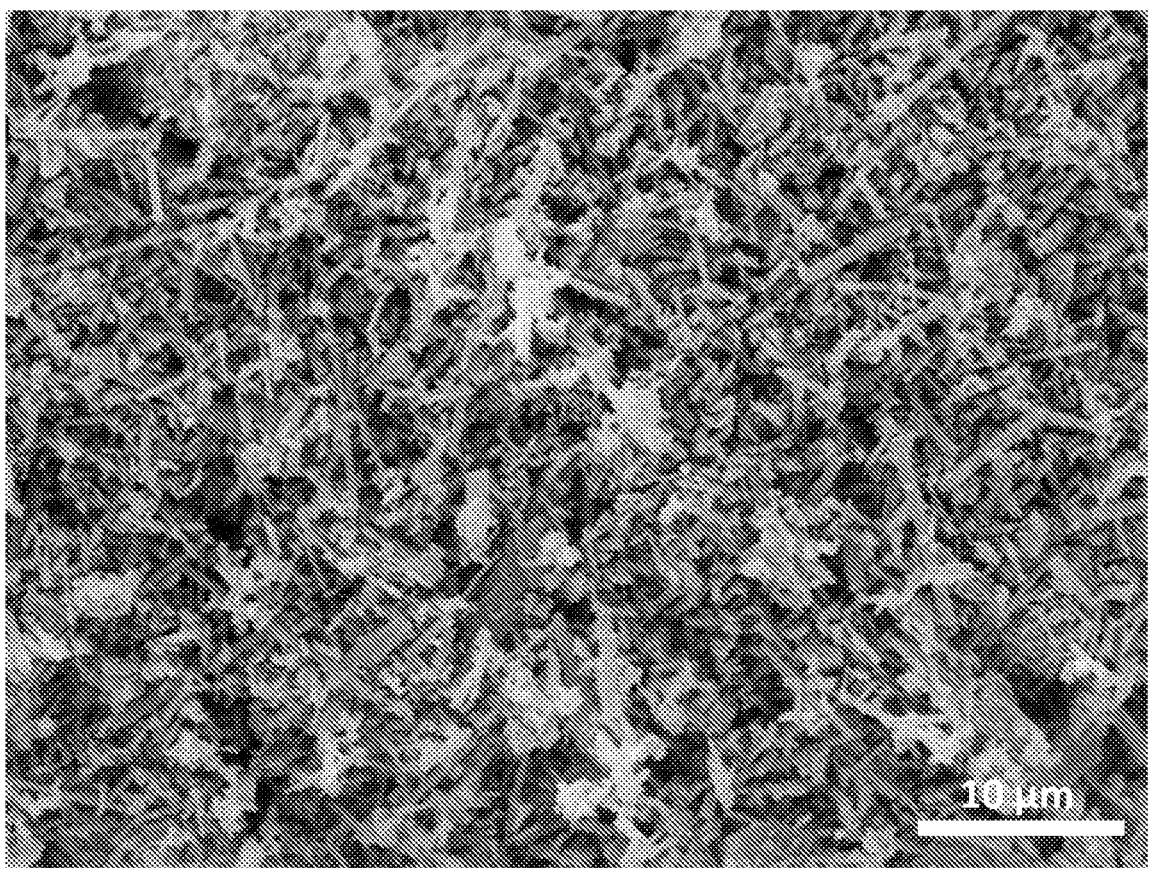
FIG. 10 shows an SEM image of Catalyst 1.1.
Figure 11:
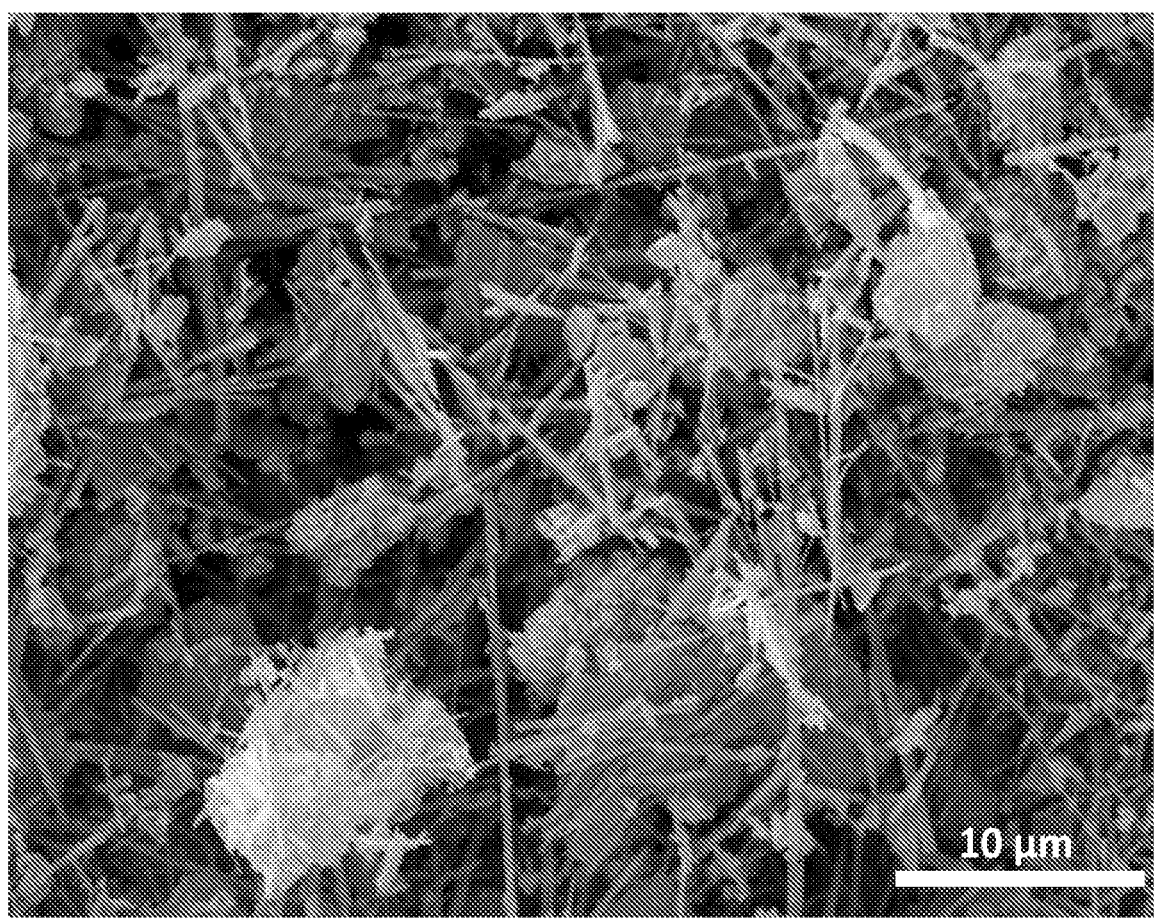
FIG. 11 shows an SEM image of Catalyst Material 1.1.
Figure 12:
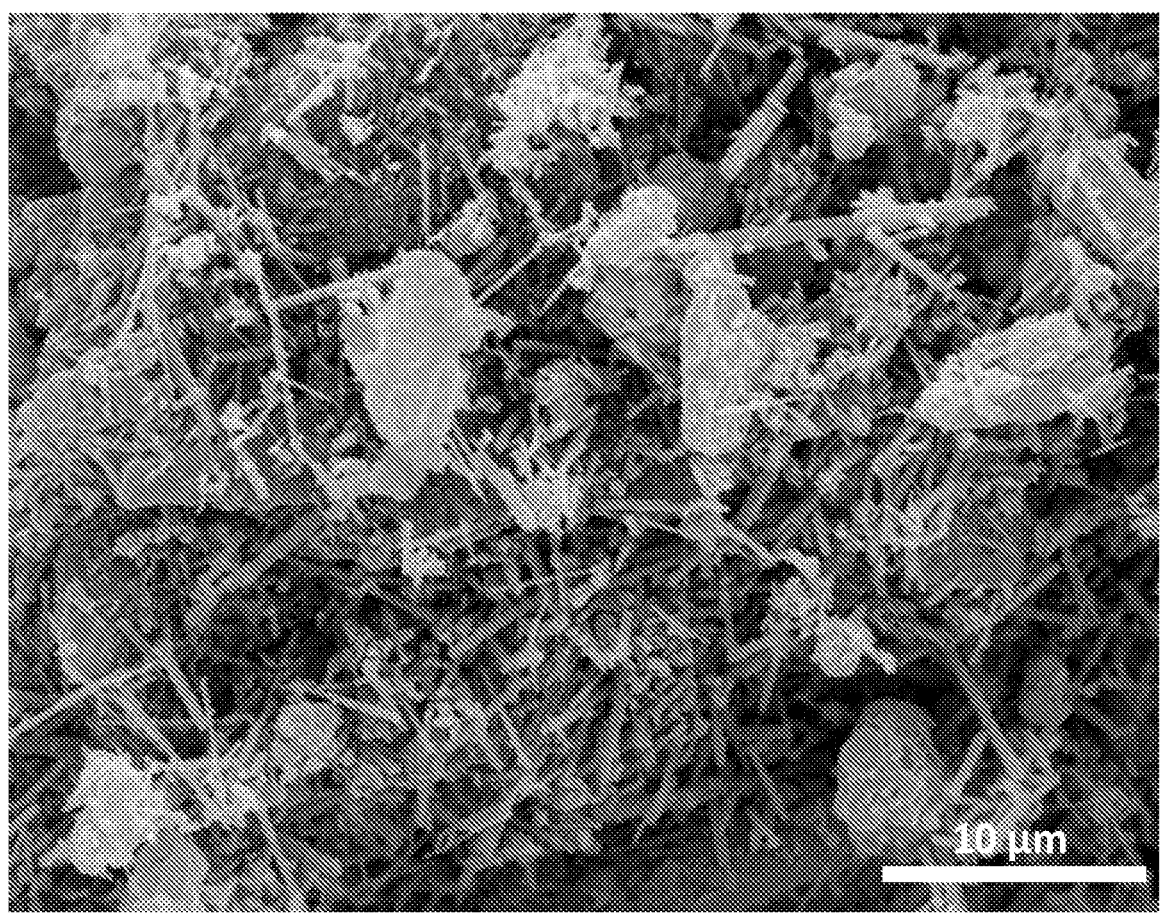
FIG. 12 shows an SEM image for Catalyst Material 1.2.

For MRU experiments, the catalyst bed was prepared by physically mixing 1.00-2.00 g of catalyst with quartz sand such that the catalyst bed had a total volume of about 6-8 mL. The catalyst bed was loaded in the middle zone of the reactor—located between points 2 and 5 of the thermocouple—and the remaining volume of the reactor was packed with quartz sand (FIGS. 9 and 10). The load was then secured with glass wool on the top and the bottom of reactor.

The gas exiting the reactor was analyzed by gas chromatography (Agilent 6890N Gas Chromatograph, using CHROMPERFECT®—Analysis, Version 6.1.10 for data evaluation) to determine the percent of various hydrocarbons (e.g., ethane and ethylene) and, optionally other gases such as $O_2$, $CO_2$, and CO and acetylene.

A catalyst or catalyst material's 35% conversion temperature was determined as follows. Conversion of the feed gas was calculated as a mass flow rate change of ethane in the product compared to feed ethane mass flow rate using the following formula:

$$C = \left(\frac{2 * X_{Ethylene} + X_{CO_2} + X_{CO}}{2 * X_{Ethylene} + 2 * X_{Ethane} + X_{CO_2} + X_{CO}}\right) * 100\%$$

In the above equation, C is the percent of feed gas that has been converted from ethane to another product (i.e., ethane conversion) and X is the molar concentration of the corresponding compound in the gaseous effluent exiting the reactor at corresponding temperature. The ethane conversion was then plotted as a function of temperature to acquire a linear algebraic equation. The linear equation for ethane conversion was solved to determine the temperature in which the ethane conversion was 35% (i.e. the 35% conversion temperature).

Further, the gas exiting the reactor was analyzed by gas chromatography to determine catalyst selectivity to ethylene (i.e., the percentage on a molar basis of ethane that forms ethylene). Selectivity to ethylene was determined using the following equation:

$$S_{Ethylene} = \left(\frac{2 * X_{Ethylene}}{2 * X_{Ethylene} + X_{CO2} + X_{CO}}\right) * 100\%$$

In the above equation, $S_{Ethylene}$ is the selectivity to ethylene and X is the molar concentration of the corresponding compound in the gaseous effluent exiting the reactor at corresponding temperature. The selectivity to ethylene was determined at the 35% conversion temperature, unless otherwise indicated. As such, after the 35% conversion temperature was determined, the above equation for selectivity was solved using the corresponding values for $X_{Ethylene}$, $X_{CO_2}$, and $X_{CO}$ at the 35% conversion temperature.

When reported, acetic acid production was determined by running MRU testing long enough to collect an aqueous condensate in the condenser (e.g., 1-3 days). After collecting a sample of the condensate, the sample was submitted for liquid GC analysis (Agilent 6890N Gas Chromatograph, Using CHROMPERFECT®—Analysis, Version 6.1.10 for data evaluation). To perform the liquid GC analysis, 300-450 mg of liquid sample was transferred to a scintillation vial. Next, 25 mg of isopropanol (IPA) was added as an internal standard. Further, 18-20 mL of distilled $H_2O$ was added to dilute the sample. Prepared samples were then transferred to GC vials and set in sequence to tested using an auto sampler. The GC analysis was a split injection method with a temperature program and FID detector. Further, a set of 3 calibration standards were run in duplicate for the relative response factor used for calculating acetic acid content in sample.

For MRU experiments, the catalyst bed was prepared by Method A or Method B.

Method A: Any added beryllium oxide was considered part of the catalyst weight loading. Catalyst weight loadings and gas flows are kept the same (2.00 g and a WHSV of 2.9 $h^{-1}$). Catalyst bed volumes are kept constant at 6 mL. This method was used for the loading and running of Catalyst 1.1 as well as $MoVBeO_x$ catalyst materials.

Method B: Any added aluminum oxide was not considered part of the catalyst weight loading. For example, if the catalyst material includes aluminum oxide in a 60 to 40 weight percentage ratio ($MoVBeO_x$ wt. % to $AlO_x$ wt. %), the typical loading of 2.00 was divided by 0.6 to calculate the target Method B loading of: 3.33 g. Catalyst bed volumes were in the range of 5 mL to 8 mL, depending on the density. Catalyst weight loadings and gas flows are kept the same (2.00 g and a WHSV of 2.9 $h^{-1}$). This method was used for the $MoVBeAlO_x$ catalyst materials, whereby no diluent was required as the mixture had 80% alumina in the mixture. Both sand and aluminum oxide are considered to be inert for the purposes of this MRU method.

All catalyst materials with added aluminum oxide in this study were loaded in Method B. When Method B was used for $MoVBeAlO_x$ catalyst material, the beryllia was considered for catalyst weight loading and any additional aluminum oxide was not considered for catalyst weight loading. Therefore, for a catalyst material was prepared from 40 wt. % alumina (e.g. boehmite), 57.9 wt. % $MoVO_x$ and 2.1 wt. % beryllia, then 60% of the resulting catalyst material was considered for catalyst weight loading. Again, catalyst weight loadings and gas flows are kept the same (2.00 g and a WHSV of 2.9 $h^{-1}$).

Acetic acid conversions were not measured on the GC because this product condenses out in the water product, where water was a product of the ODH process. Additionally, not enough aqueous acetic acid condensate was produced during an MRU screening run (single day run) to be accurate quantified by GC. Longer collection times (roughly x time) were required to quantify the amount of acetic acid produced as byproduct.

ICP-MS

Samples were prepared according to one of the following two digestion methods:

Sodium Hydroxide Preparation

Digestion of sample was conducted to bring the sample into solution prior to dilution in nitric acid. Sample (10 mg) was placed into a scintillation vial with 3 mL sodium hydroxide solution (6.25 mol/L). The sample solution was stirred via stir-bar in a 90° C. oil bath. Once the sample was digested, the solution was transferred into an ICP-MS containment vessel with the scintillation vial being rinsed three times with a total of 15 mL ICP grade water. The rinses are added to the ICP-MS containment vessel. The solution was then brought up to 25 mL with ICP grade water. The solution was analyzed via ICP-MS. Weights are recorded throughout the preparation process to be entered into the ICP-MS software for result calculations.

Lithium Metaborate Fusion Preparation

Fusion of sample was conducted for amalgamation prior to dissolving\dilution in nitric acid. Sample (10 mg) was placed into a platinum crucible with 0.1 g Lithium metaborate (98.5%)/Lithium Bromide (1.5%) covering the sample. The crucible was placed into a muffle furnace at room temperature and brought up to 1000° C. over 2 hours. Once at 1000° C., the sample remains in the muffle furnace for 20 minutes before the temperature program was turned off. The sample cools down in the muffle furnace until the muffle furnace reaches 500° C., at which point the crucible was removed and placed at a cooling station to continue to cool to room temperature. The crucible with amalgamated sample was placed on a stir plate and slowly stirred via stir-bar with 5 mL 5% nitric acid for 2 hours to dissolve the sample into solution. The solution was transferred into an ICP-MS containment vessel with the crucible being rinsed three times with a total of 15 mL 5% nitric acid. The rinses are added to the ICP-MS containment vessel. An additional 100× dilution with 5% nitric acid was conducted prior to analysis via ICP-MS. Weights are recorded throughout the preparation process to be entered into the ICP-MS software for result calculations.

XRD Analysis

Powder X-Ray Diffractometry (PXRD) data was collected using a PANalytical Aeris X-ray diffractometer by SEMx Incorporated. This diffractometer instrument consisted of three basic elements: X-ray tube, sample holder, and X-ray detector. X-rays were generated in a cathode ray tube (Cu source with Kα radiation=1.5418 Å) with the resulting X-rays being directed onto the sample. As the sample and detector are rotated, the intensity of the reflected X-rays was recorded to produce characteristic X-ray spectra. When the incident X-rays reflecting off the sample satisfies the Bragg Equation (nλ=2d sin θ), constructive interference occurs and a peak in intensity occurs (y-axis). X-ray diffractometers were setup such that the sample rotates in the path of the X-ray beams at an angle θ, while the X-ray detector was mounted on an arm to collect the diffracted X-rays and rotates at an angle of 2θ from ~5° to 70° (x-axis).

Qualitative XRD analysis and Rietveld Refinement was performed using HighScore Plus XRD analysis software. The samples were finely ground to reduce particle size and to obtain a uniform mixture. They were then loaded onto the XRD sample holder and the XRD spectrum was acquired. The Rietveld Refinement results were combined with Highscore Plus and EDS results to perform qualitative and quantitative analysis.

The weight percentage of amorphous content was determined by external standard. With an external standard phase, the instrument intensity constant, K-factor, was determined. Corundum was used as the external standard and was measured with the same instrument configuration shortly after the unknown sample was measured. The K-factor approach is described by O'Connor and Raven: 1988, Powder Diffraction, 3 (1), 2-6. For each sample, the weight percentage of the crystalline $MoVO_x$ orthorhombic phase had to be determined in order to assign weight percentages to the amorphous content. The Degree of Crystallinity (DOC) Method, based on the estimation that the total intensity of area contributed to the overall diffraction pattern by each component in the analysis, was used to determine the amount of amorphous phase. The degree of crystallinity was calculated from the total areas under the defined crystalline and amorphous components from:

DOC=Crystalline Area Crystalline Area+Amorphous Area

Where the weight fraction of the amorphous material was calculated from:
Wamorphous=1−DOC
Comparative Raw Data Analysis The PXRD raw data was also analyzed using a Python code through the program Spyder. The code generated overlaid plots. It also analyzed the data by comparing the peak prominence of all the local maxima and generated a plot with peaks meeting an established threshold. Relevant catalyst peaks are highlighted in the plot with vertical lines and the range of the relative peak intensities were provided by the code.

SEM

Scanning electron microscope (SEM) images were collected using a JSM-IT300LV INTOUCHSCOPE™. Samples were prepared on an aluminum stud with double sided carbon tape.

SEM-EDS

Energy-dispersive X-ray spectroscopy (EDS) was conducted using a JEOL JED-2300 DRY SDD EDS detector. Samples were sent to SEMx Incorporated for EDS analysis. The samples were finely ground to reduce particle size and obtain the uniform mixture. They were then loaded onto EDS stub for analysis by SEM. EDS was used for elemental analysis and surface examination. EDS is a micro-analytical technique that provides a semi-quantitative elemental analysis of the surface of a sample (e.g., the top 1 to 3 microns). The SEM was used to examine the surface morphology at magnifications ranging from 20 to 100,000 times. The EDS instrument detects elements with an atomic number equal or greater than sodium, but also has light element capability, which means that it can also detect carbon, nitrogen, oxygen, and fluorine. The estimated lower detectable limit for any given element generally is between about 0.2 and 0.5 wt. %.

PSD by SEM

Samples were sent to SEMx Incorporated for particle size analysis using scanning electron microscopy (SEM), model JEOL-JSM300 LV. SEM was used to observe and count the particles in the sample to obtain the Particle Size Distribution (PSD). For the PSD measurements, the SEM instrument took pictures at different magnifications. Measurements were done for 400-800 particles at different magnifications to cover the size range (statistical population). Size was measured by length in micrometers and was measured on the longest dimension of the particles. SEM based PSD is a method for analyzing samples where particles are agglomerated (stuck together) because the analyst can visually see this through the microscope and make the judicious decision to measure the distinct particles rather than the agglomerates. Statistics and analysis were based on total counts measured by SEM.

Yield Calculations

Theoretical yield calculations were based on the weight of each reagent used.

The weight of each reagent used in grams was divided by the molecular weight in grams per mol. For example:

Weight $(NH_4)_6Mo_7O_{24} \cdot 4H_2O$ (g)/Molecular weight $(NH_4)_6Mo_7O_{24} \cdot 4H_2O$ (g/mol)= $(NH_4)_6Mo_7O_{24} \cdot 4H_2O$ mol This calculation was performed for the vanadium as well.

The theoretical moles of the final product were calculated by assuming that both the molybdenum and the vanadium have attained the highest oxidation states in the final product. Thus, molybdenum and vanadium formed $MoO_3$ and $V_2O_5$ respectively. For example:

$1(NH_4)_6Mo_7O_{24} \cdot 4H_2O \rightarrow 7MoO_3$ $1VOSO_4 \cdot 3.46H_2O \rightarrow \frac{1}{2}V_2O_5$ The moles of the starting material were used and multiplied by the respective molar equivalents of each of the total oxidized species. The moles were then multiplied by the predicted theoretical weight of the fully oxidized final product in order to get the final theoretical weight of the catalyst. For example:

Theoretical weight of molybdenum in the fully oxidized state:

$(NH_4)_6Mo_7O_{24} \cdot 4H_2O$ mol×7=7($MoO_3$ mol)

(($MoO_3$ mol))×$MoO_3$ g/mol=Theoretical weight of fully oxidized molybdenum in grams Theoretical weight of vanadium in the fully oxidized state:

$(VOSO_4 \cdot 3.46H_2O$ mol×$\frac{1}{2}$=$\frac{1}{2}V_2O_5$ mol)

($V_2O_5$ mol×$V_2O_5$ g/mol)=Theoretical weight of fully oxidized vanadium in grams Total theoretical weight in g=(Theoretical weight of fully oxidized molybdenum in grams)+(Theoretical weight of fully oxidized vanadium in grams)

Percent yield=(Actual measured yield (g)/Theoretical yield (g))×100

The percent yield was determined by diving the actual measured yield by the theoretical yield and multiplying by 100.

Crush Strength Testing

The crush strength testing was done with the use of the standard ASTM method D4179-11, Standard Test Method for Single Pellet Crush Strength of Formed Catalyst and Catalyst Carriers using a Torbal force gauge FB500. The maximum force capacity of the gauge was 500 N with a resolution of 0.1N.

Bulk Density Measurement

To a 10 mL graduated cylinder. The graduated cylinder was tarred and filled to the 10 mL mark with pelletized catalyst. The graduated cylinder was tapped such that the pelletized catalyst settled in the cylinder. The weight of the catalyst that fits in the cylindrical 10 mL portion was recorded. This weight was divided by 10 mL to get the bulk density measurement.

MRU Results

Figure 2:
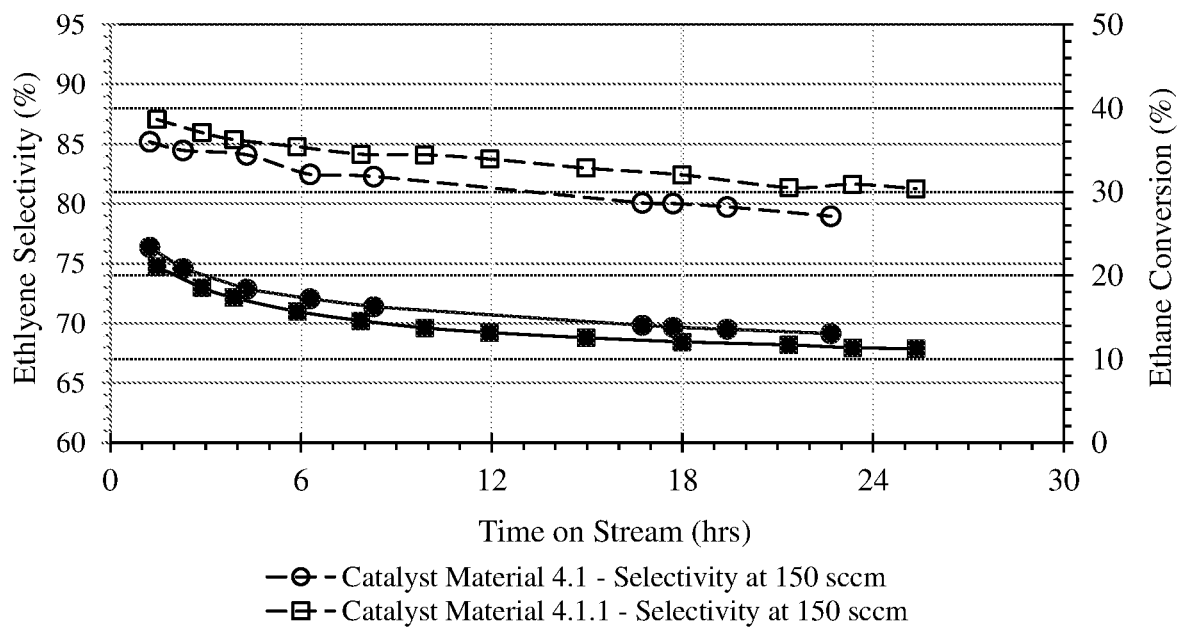
FIG. 2 shows overlaid MRU raw data for Catalyst Material 4.1 and Catalyst Material 4.1.1.

The MRU 35% ethane conversion results for select samples, as well as beryllium oxide powder and calcium carbonate powder are presented in Table 1, Table 2, Table 3, and Table 4. The overlaid MRU performance for Catalyst Material 2.4 and Catalyst Material 2.6 is presented in FIG. 1. The 24 h+ collection of data in FIG. 1 is experimentally equivalent given experimental error. The overlaid MRU performance for Catalyst Material 4.1 and Catalyst Material 4.1.1 is presented in FIG. 2. The data presented in FIG. 2 shows that the addition of 5% calcium carbonate to Catalyst Material 4.1 via the "dry mixing method" (Catalyst Material 4.1.1) provided a slight increase in selectivity comparatively to Catalyst Material 4.1. This improvement in selectivity comes with a slight decrease in activity. The addition of calcium carbonate is beneficial for pressing the Catalyst Material (4.1 vs 4.1.1), without damaging the die sets.

TABLE 1

| Samples | Temperature at 35 mol. % Ethane Conversion (° C.) | Ethylene Selectivity at 35 mol. % Conversion Temperature (%) | Sample Loading in MRU Reactor (g) | Gas Feed Flow (sccm) | Gas Feed composition (%) | | | Delta T ‡ (° C.) | $R^2$ factor of interpolated results | |
|---|---|---|---|---|---|---|---|---|---|---|
| | | | | | $C_2$ | $O_2$ | $N_2$ | | Conversion | Selectivity |
| Beryllium Oxide powder | >>380 † | — | 2.0052 | 76.1 | 36.1 | 16.2 | 47.7 | — | — | — |
| Calcium Carbonate powder | >>380⸰ | — | 1.9983 | 76.1 | 36.1 | 16.2 | 47.7 | — | — | — |
| Catalyst 1.1 | 341 | 87 | 2.01 | 76.1 | 34.6 | 16.5 | 45.6 | — | 1.00 | 1.00 |
| Catalyst Material 1.1 | 325 | 88 | 1.9937 | 76.1 | 34.6 | 16.5 | 45.6 | −17 | 1.00 | 0.99 |
| Catalyst Material 1.2 | 327 | 90 | 5.0054 | 76.1 | 34.6 | 16.5 | 45.6 | −14 | 0.99 | 0.82 |

† Temperature of 380° C. provided 0.29 mol. % ethane conversion. No higher conversion could be obtained through direct measurement.
⸰ Temperature of 380° C. provided 0.21 mol. % ethane conversion. No higher conversion could be obtained through direct measurement.
‡ Delta T (° C.) is defined as the difference between the 35% conversion temperature relative to Catalyst 1.1.

TABLE 2

| Samples | Temperature at 35 mol. % Ethane Conversion (° C.) | Ethylene Selectivity at 35 mol. % Conversion Temperature (%) | Sample Loading in MRU Reactor (g) | Gas Feed Flow (sccm) | Gas Feed composition (%) | | | Delta T ‡ (° C.) | $R^2$ factor of interpolated results | |
|---|---|---|---|---|---|---|---|---|---|---|
| | | | | | $C_2$ | $O_2$ | $N_2$ | | Conversion | Selectivity |
| Catalyst 1.2 | 353 | 82 | 2.0870 | 76.1 | 34.6 | 16.5 | 45.6 | — | 1.00 | 1.00 |
| Catalyst Material 2.1 | 344 | 88 | 4.9980 | 76.1 | 34.6 | 16.5 | 45.6 | −9 | 0.99 | 0.92 |
| Catalyst Material 2.2.1 | 347 | 87 | 4.9971 | 76.1 | 36.2 | 17.2 | 46.4 | −6 | 1.00 | 1.00 |
| Catalyst Material 2.4* | 359 | 88 | 5.0006 | 38.0 | 36.5 | 16.0 | 48.4 | 6 | 1.00 | 1.00 |
| Catalyst Material 2.5.1 | 389 | 80 | 5.0062 | 38.0 | 37.1 | 17.9 | 44.9 | 36 | 0.86 | 1.00 |
| Catalyst Material 2.6 | 345 | 87 | 5.0087 | 38.0 | 35.5 | 16.3 | 48.1 | −8 | 1.00 | 1.00 |

‡ Delta T (° C.) is defined as the difference between the 35% conversion temperature relative to Catalyst 1.2.
*Only two MRU data points used to establish data set. More performance data is presented in FIG. 1.
Note:
35% ethane conversion temperatures reported above 380° C. are extrapolated, not interpolated.

TABLE 3

| Samples | Temperature at 35 mol. % Ethane Conversion (° C.) | Ethylene Selectivity at 35 mol. % Conversion Temperature (%) | Sample Loading in MRU Reactor (g) | Gas Feed Flow (sccm) | Gas Feed composition (%) | | | Delta T ‡ (° C.) | $R^2$ factor of interpolated results | |
|---|---|---|---|---|---|---|---|---|---|---|
| | | | | | $C_2$ | $O_2$ | $N_2$ | | Conversion | Selectivity |
| Catalyst 1.3 | 356 | 82 | 2.0008 | 76.1 | 34.6 | 16.5 | 46.6 | — | 1.00 | 0.59 |
| Catalyst Material 3.1 | 335 | 88 | 1.9928 | 76.1 | 35.8 | 17.1 | 47.1 | −21 | 1.00 | 0.99 |
| Catalyst Material 3.1.1 | 336 | 89 | 5.0003 | 76.1 | 36.2 | 16.4 | 47.4 | −20 | 1.00 | 1.00 |

TABLE 3-continued

| Samples | Temperature at 35 mol. % Ethane Conversion (° C.) | Ethylene Selectivity at 35 mol. % Conversion Temperature (%) | Sample Loading in MRU Reactor (g) | Gas Feed Flow (sccm) | Gas Feed composition (%) | | | Delta T ‡ (° C.) | $R^2$ factor of interpolated results | |
|---|---|---|---|---|---|---|---|---|---|---|
| | | | | | $C_2$ | $O_2$ | $N_2$ | | Conversion | Selectivity |
| Catalyst Material 3.2.1 | 699 | 54 | 4.9894 | 76.1 | 35.0 | 16.7 | 48.3 | 343 | 0.98 | 0.77 |
| Catalyst Material 3.2.2 | 1112 | † | 5.0041 | 76.1 | 35.2 | 17.0 | 47.8 | 756 | 1.00 | 1.00 |
| Catalyst Material 3.3.1 | 406 | 86 | 4.9887 | 76.1 | 36.8 | 16.8 | 46.4 | 50 | 1.00 | 0.99 |
| Catalyst Material 3.3.2 | 558 | 81 | 4.9972 | 76.1 | 36.5 | 17.2 | 46.2 | 202 | 0.80 | 0.18 |
| Catalyst Material 3.4.1 | 1193 | † | 6.9870 | 76.1 | 35.7 | 17.0 | 47.3 | 837 | 0.98 | 0.86 |
| Catalyst Material 3.4.2 | — | — | — | — | — | — | — | — | — | — |

† value obtained from linear algebraic expression was below zero.
‡ Delta T (° C.) is defined as the difference between the 35% conversion temperature relative to Catalyst 1.3.
35% ethane conversion temperatures reported above 380° C. are extrapolated, not interpolated.

TABLE 4

| Samples | Temperature at 35 mol. % Ethane Conversion (° C.) | Ethylene Selectivity at 35 mol. % Conversion Temperature (%) | Sample Loading in MRU Reactor (g) | Gas Feed Flow (sccm) | WHSV (1/h) | Gas Feed composition (%) | | | Delta T ‡ (° C.) | $R^2$ factor of interpolated results | |
|---|---|---|---|---|---|---|---|---|---|---|---|
| | | | | | | $C_2$ | $O_2$ | $N_2$ | | Conversion | Selectivity |
| Catalyst 4.1 | 353 | 82 | 2.0001 | 76.1 | 2.79 | 34.6 | 16.5 | 45.6 | — | 0.99 | 0.03 |
| Catalyst Material 4.1 | 361 | 87 | 7.4999 | 57 | 2.79 | 37.0 | 17.3 | 45.5 | — | 0.86 | 0.77 |
| Catalyst Material 4.1 | 447 | 78 | 6.0002 | 150 | 9.16 | 35.5 | 17.5 | 47.0 | — | 1.00 | 0.98 |
| Catalyst Material 4.1.1 | 461 | 79 | 6.0002 | 150 | 9.16 | 35.1 | 17.3 | 47.6 | — | 1.00 | 0.99 |

‡ Delta T (° C.) is defined as the difference between the 35% conversion temperature relative to Catalyst 1.4.
Note:
35% ethane conversion temperatures reported above 380° C. are extrapolated, not interpolated.

Elemental Analysis

The ICP-MS analysis and EDS analysis for Catalyst 1.1 as well as Catalyst Materials 1.1 and 1.2 are presented in Table 5. EDS is not well suited for identifying elements lighter than Na. As such, the contents of Be cannot be identified by this technique. Ranges were established by assuming all of the alumina was either AlOOH or $Al_2O_3$. Catalyst base material ranges were established from ICP-MS measurements of various catalyst active phase batches.

TABLE 5

| | | Molar Elemental Composition of Metal Oxide Mixtures | | |
|---|---|---|---|---|
| Sample | Digestion Method | ICP-MS and calculation | EDS | Theoretical |
| Catalyst 1.1 | NaOH | $Mo_{1.00}V_{0.43}$ | $Mo_{1.00}V_{0.41}$ | $Mo_{1.00}V_{0.40-0.48}$ |
| Catalyst Material 1.1 | NaOH | $Mo_{1.00}V_{0.43}Be_{0.54}$ | $Mo_{1.00}V_{0.42}$ | $Mo_{1.00}V_{0.38-0.49}Be_{0.58-0.63}$ |
| Catalyst Material 1.2 | $Li_2B_4O_7$ | $Mo_{1.00}V_{0.40}Be_{0.60}Al_{4.08}$ | $Mo_{1.00}V_{0.41}Al_{4.02}$ | $Mo_{1.00}V_{0.38-0.49}Be_{0.58-63}Al_{4.29-5.89}$ |

SEM and PSD Analysis

Figure 3:
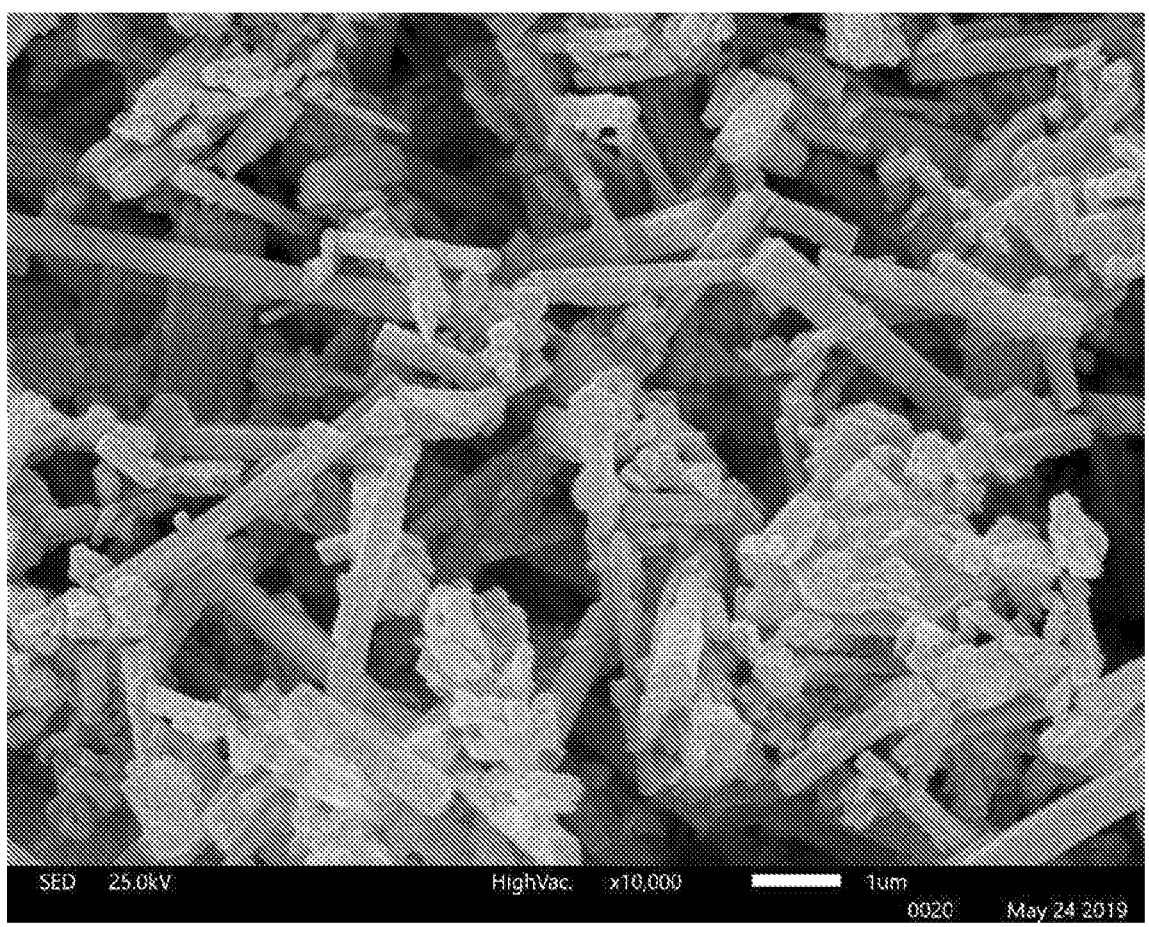
FIG. 3 shows a 10,000× magnification SEM image of Catalyst 1.1.
Figure 4:
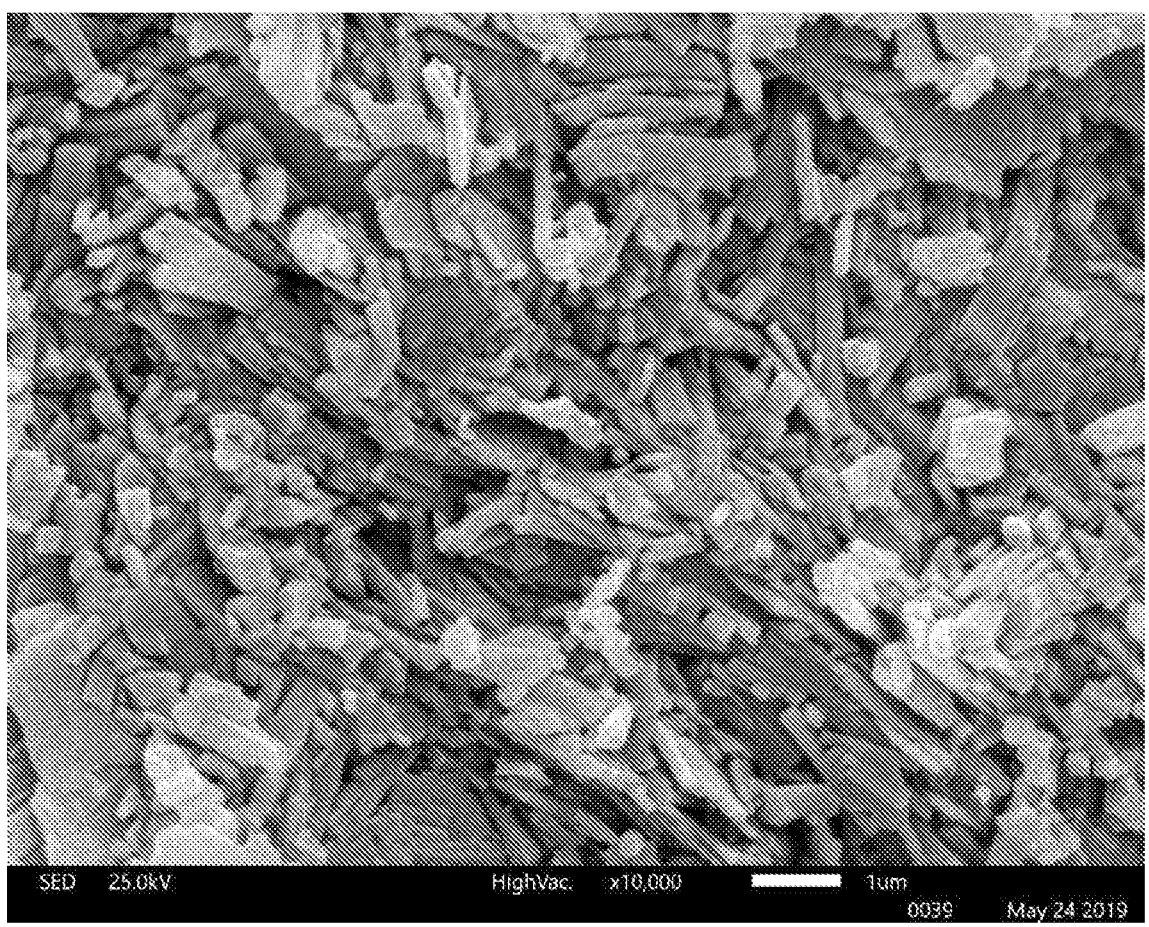
FIG. 4 shows a 10,000× magnification SEM image of Catalyst Material 1.1.
Figure 5:
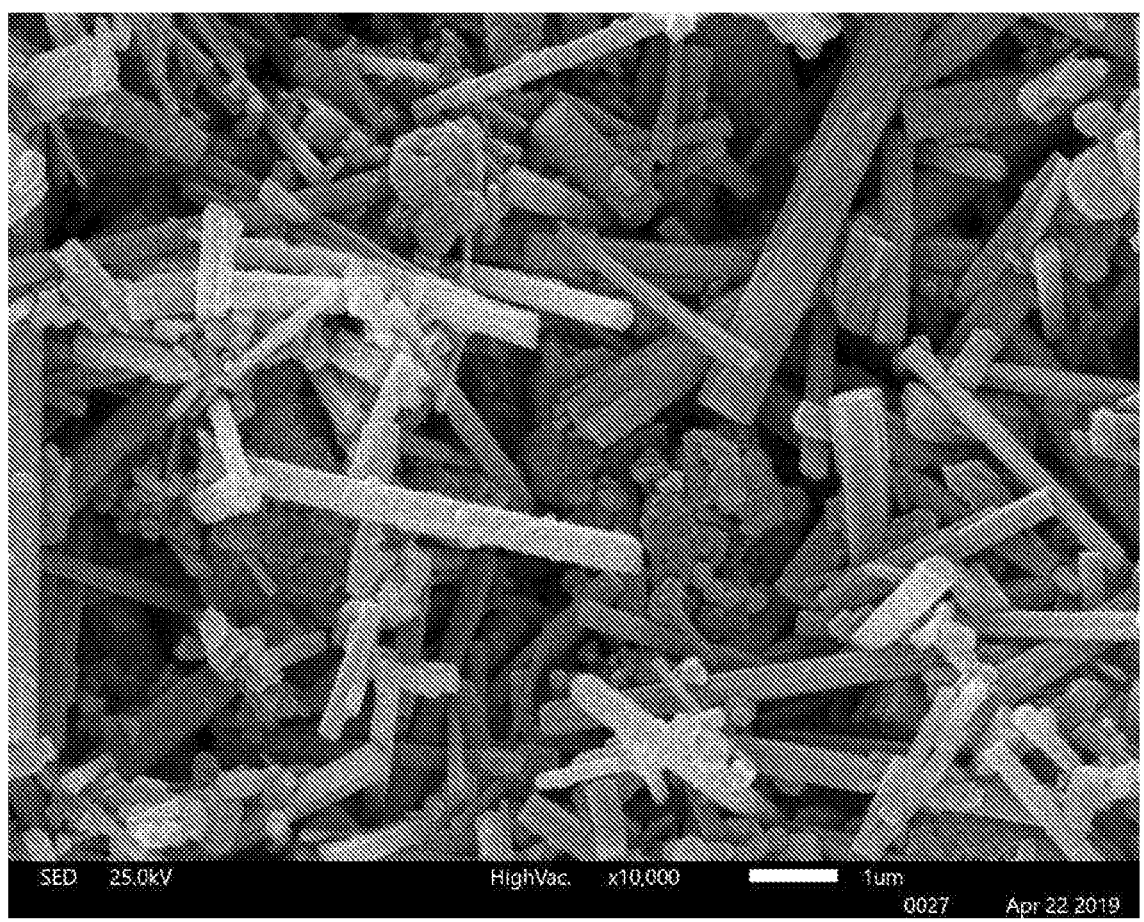
FIG. 5 shows a 10,000× magnification SEM image of Catalyst Material 1.2.
Figure 6:
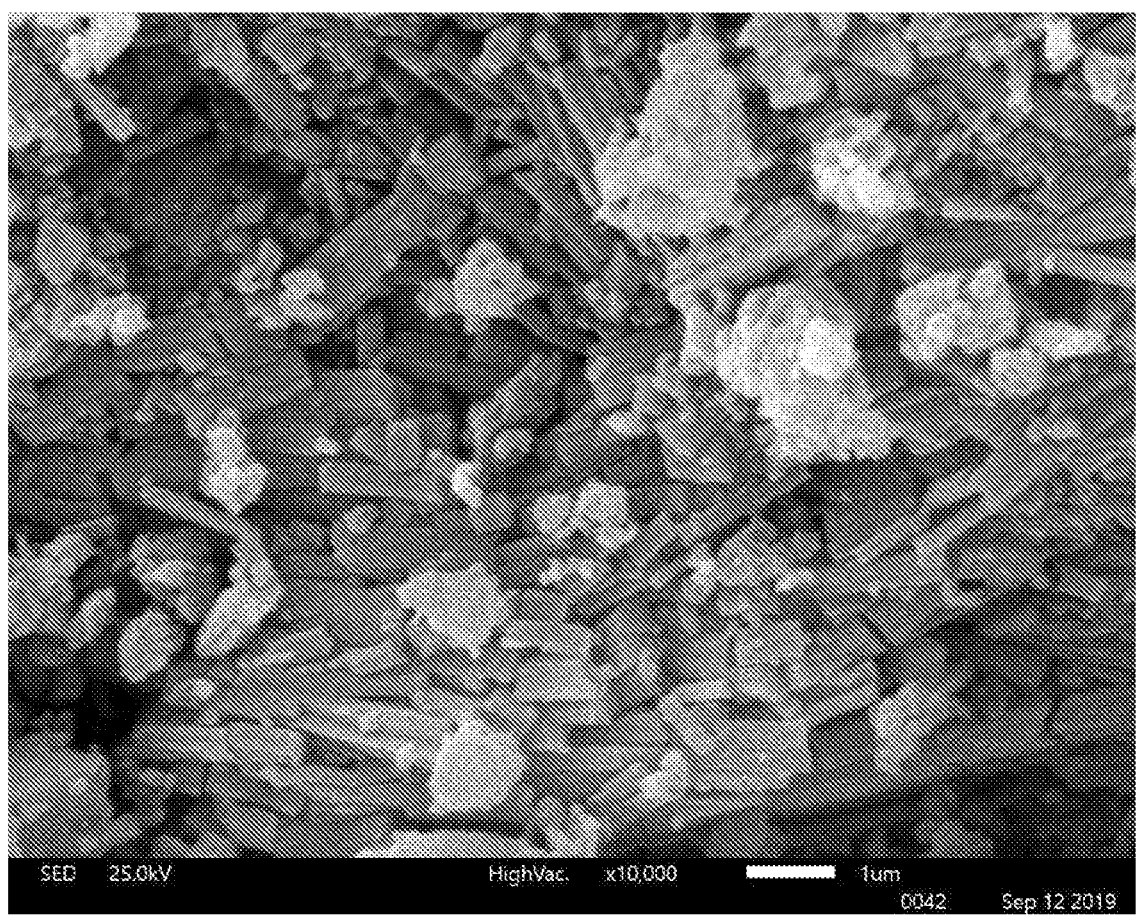
FIG. 6 shows a 10,000× magnification SEM image of Catalyst Material 2.2.1.
Figure 7:
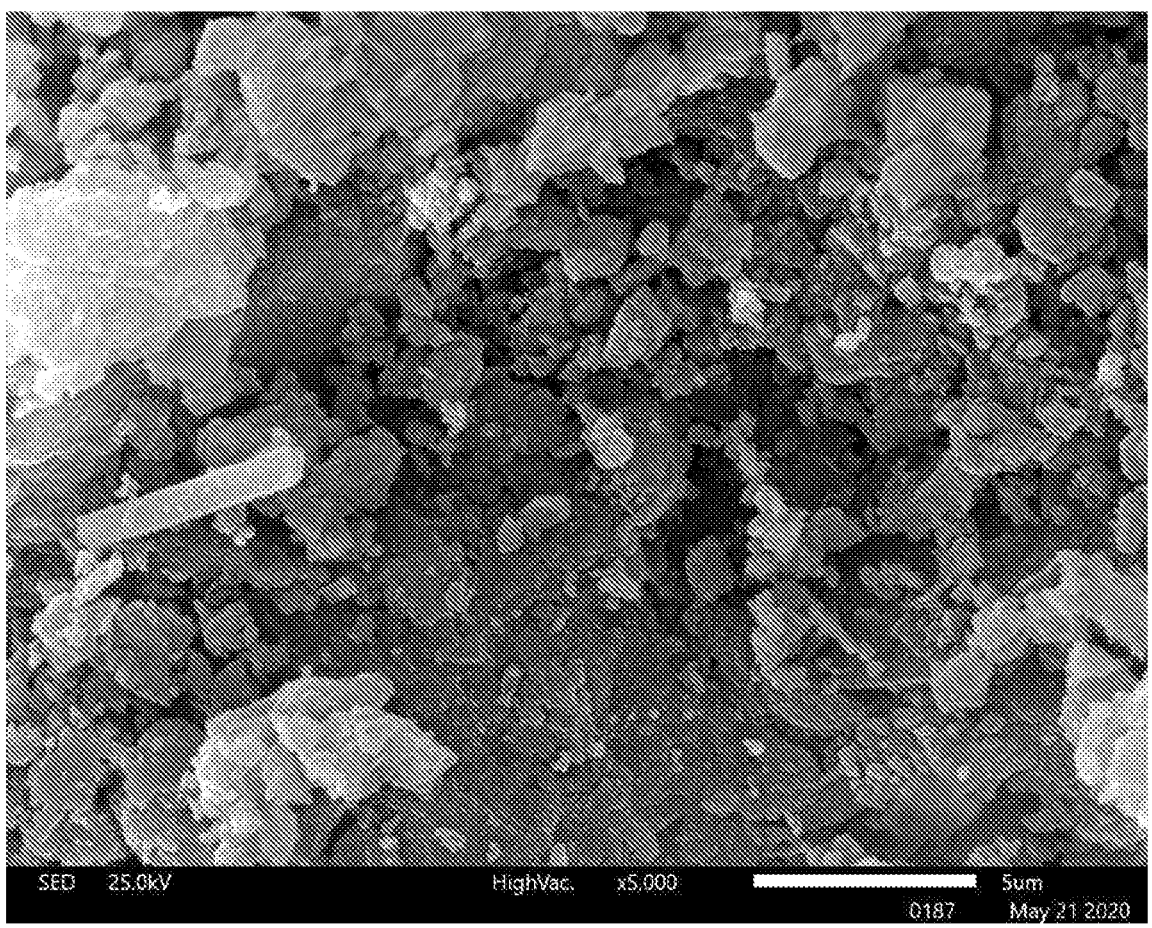
FIG. 7 shows a 5,000× magnification SEM image of Catalyst Material 2.6.
Figure 8:
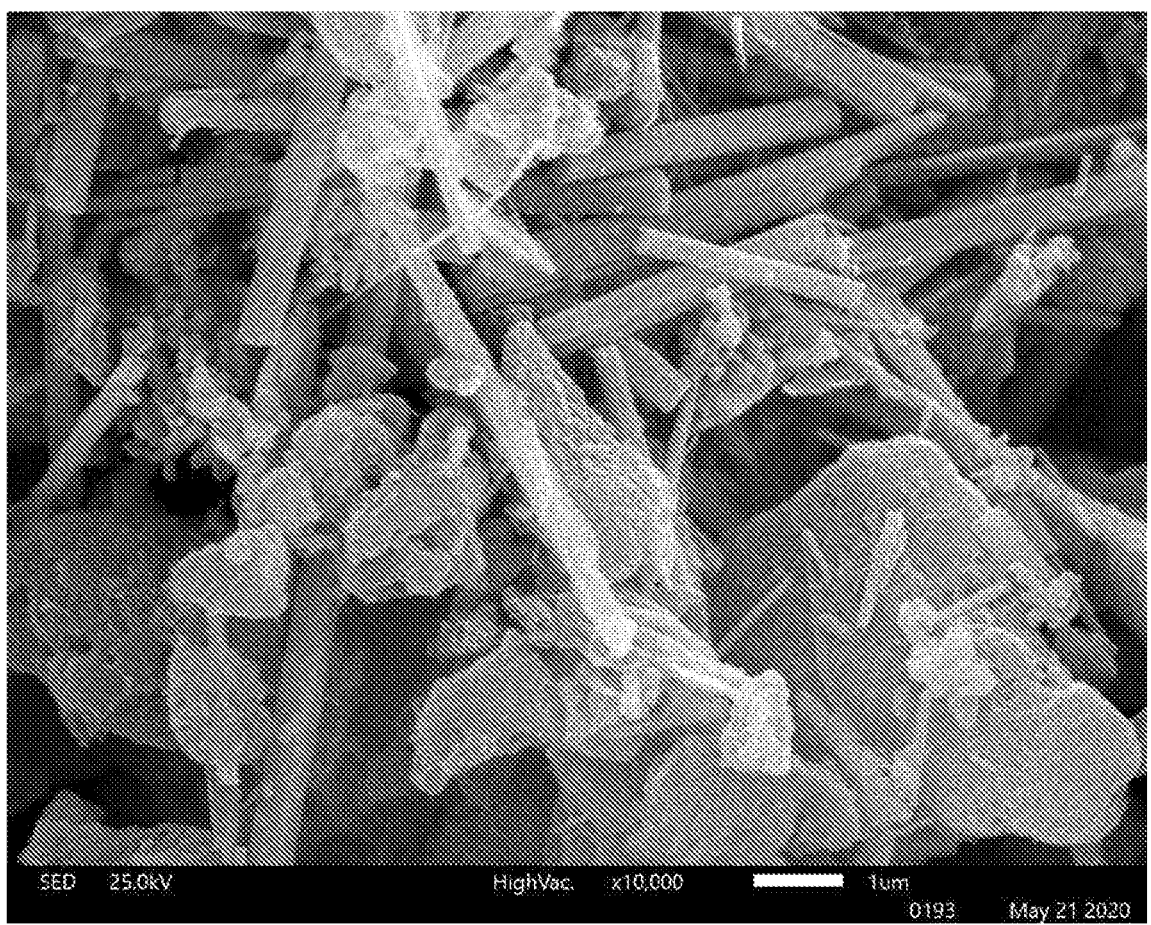
FIG. 8 shows a 10,000× magnification SEM image of Catalyst Material 2.4.

Table 6 presents the particle size analysis from SEM for Catalyst 1.1 as well as Catalyst Materials 2.1 and 2.2. The SEM image of Catalyst 1.1 at a 10,000× magnification is presented in FIG. 3. The SEM image of Catalyst Material 1.1 at a 10,000× magnification is presented in FIG. 4. The SEM image of Catalyst Material 1.2 at a 10,000× magnification is presented in FIG. 5. The SEM image of Catalyst Material 2.2.1 at a 10,000× magnification is presented in FIG. 6. The SEM image of Catalyst Material 2.4 at a 10,000× magnification is presented in FIG. 8. The SEM image of Catalyst Material 2.6 at a 5,000× magnification is presented in FIG. 7. The SEM image of BeO at a 10,000× magnification is presented in FIG. 9.

The XRD phase fitting and amorphous content analysis for Catalyst 1.1, Catalyst Materials 1.1, Catalyst Material 1.2, Catalyst Material 2.2.1, Catalyst Material 2.4, and Catalyst Material 2.6, as well as beryllium oxide and VERSAL™ 250 Alumina are presented in Table 8. The theoretical amorphous content was calculated using the amorphous content of Catalyst 1.1, BeO, and VERSAL™ alumina, and is meant to represent what amorphous content should have been observed if no phase changes occurred after the addition of promotor and support. The theoretical amorphous content could not be calculated for Catalyst Material 2.2.1 because the amorphous content of calcium carbonate was not identified. In all examples, the amorphous content increased comparatively to the theoretical amount.

TABLE 8

| Sample | M1 orthorhombic phase (wt. %) | Other metal oxide or mixed metal oxide phases (wt. %) | Amorphous content (wt. %) | Total (wt. %) | Theoretical amorphous content (wt. %) | Difference (wt. %) |
| --- | --- | --- | --- | --- | --- | --- |
| Catalyst 1.1 | 33.9 | 3.5 | 62.6 | 100.0 | — | 0 |
| Catalyst Material 1.1 | 26.2 | 14.3 | 59.4 | 99.9 | 59.1 | −0.3 |
| Catalyst Material 1.2 | 10.4 | 22.7 | 66.8 | 99.9 | 54.4 | −12.4 |
| Catalyst Material 2.2.1 | 6.5 | 20.8 | 72.6 | 99.9 | — | — |
| Catalyst Material 2.4 | 2.3 | 43.6 | 54.2 | 100.1 | 52.8 | −1.7 |
| Catalyst Material 2.6 | 1.6 | 40.3 | 58.1 | 100.0 | 52.8 | −5.6 |
| BeO | — | 80.63 | 19.37 | 100.0 | — | — |
| VERSAL ™ 250 Alumina | — | 48.8 | 51.2 | 100.0 | — | — |

TABLE 6

| Sample | Mean Particle Size (μm) |
| --- | --- |
| Catalyst 1.1 | 1.98 |
| Catalyst Material 1.1 | 4.16 |
| Catalyst Material 1.2 | 9.20 |

XRD Analysis

Figure 14:
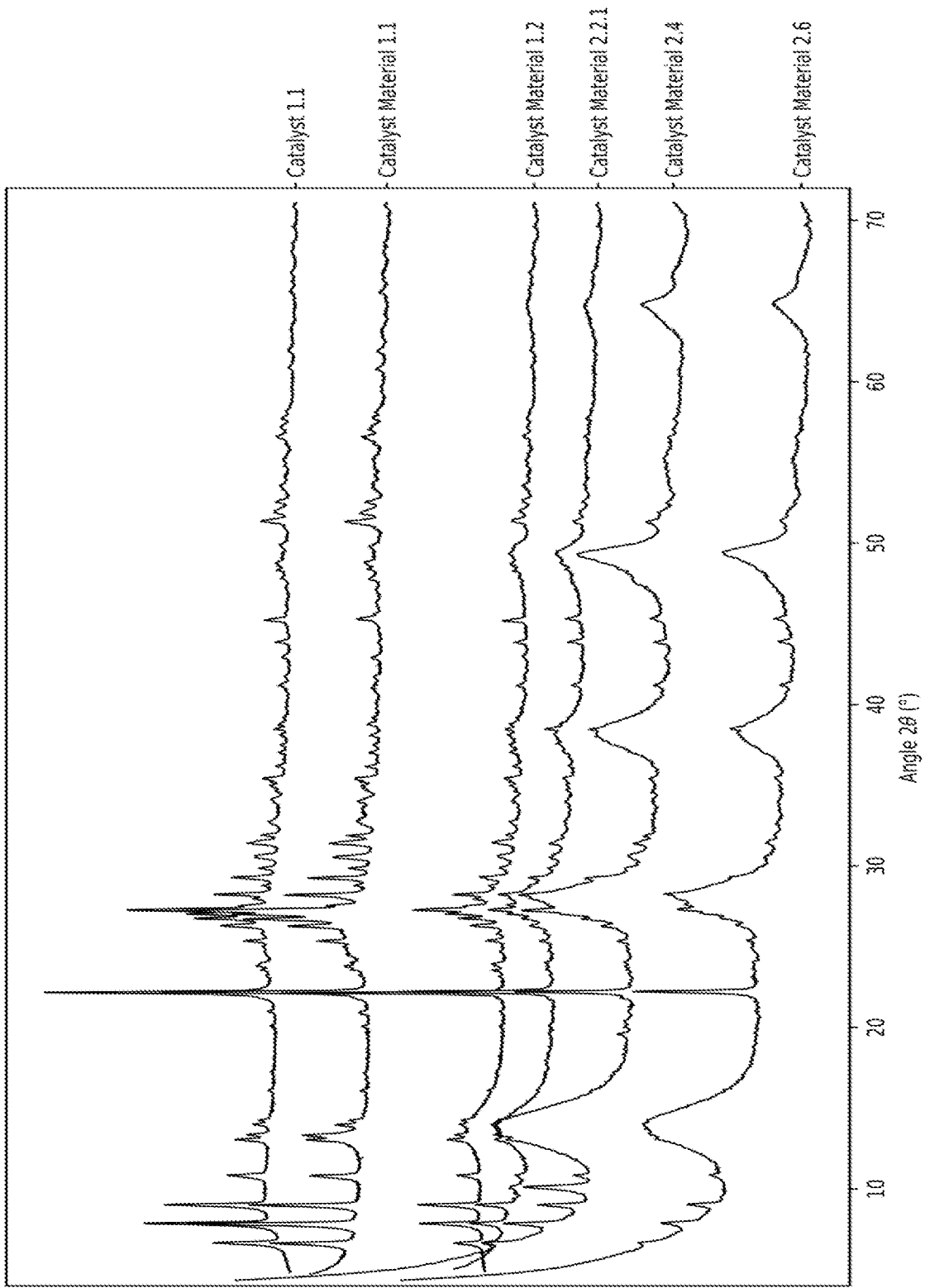
FIG. 14 shows overlaid PXRD diffractograms Catalyst 1.1, Catalyst Material 1.1, Catalyst Material 1.2, Catalyst Material 2.2.1, Catalyst Material 2.4, and Catalyst Material 2.6.

PXRD diffractograms for Catalyst 1.1, Catalyst Material 1.1, Catalyst Material 1.2, Catalyst Material 2.2.1, Catalyst Material 2.4, and Catalyst Material 2.6 are presented in FIG. 14.

Table 7 presents the crystallite size for Catalyst 1.1, Catalyst Material 1.1, and Catalyst Material 1.2, which was calculated by the Scherrer equation, using the main peak at 22.1 Rad 2Θ, and the raw data from the PXRD diffractograms. Since this peak in indicative of the M1/M2 phase (and possibly other mixed metal oxide phases), the reported crystallite sizes only reflect the crystalline phases. Addition of BeO to Catalyst 1.1 resulted in a decrease in crystallite size. However, addition of alumina to Catalyst Material 1.1 resulted in an increase the crystallite size, even comparatively to Catalyst 1.1. This could suggest that the promoter and support interact with the crystalline phases.

TABLE 7

| Sample | Crystallite Size (nm) |
| --- | --- |
| Catalyst 1.1 | 128.52 |
| Catalyst Material 1.1 | 112.46 |
| Catalyst Material 1.2 | 149.44 |

M1 orthorhombic phase is identified as a phase fitted with either 04-022-1665 or 04-022-1664, or a combination of both.

Analysis of the final formulated catalyst material by XRD and SEM, indicated that promoting and supporting the $MoVO_x$ catalyst with beryllium and aluminum oxides respectively is accompanied by a change in crystallinity, as shown in Table 8. The crystallinity of the overall mixture significantly decreases, which implies that a recrystallization or phase transition has occurred during the wet mixing process. The resulting active phase crystal size and overall particle size also increased as a result (Table 6, Table 7). The phase transition is surprising as it would not be expected that a simple wet mixing of metal oxides would be accompanied by a change in crystallinity. This is likely due to the alumina and baseline catalyst interaction causing a recrystallization of the catalyst mixture. This in turn increases the crystal size which increases the overall particle size of the catalyst, beryllium and aluminum oxide mixture.

A Python code (scipy.singal.find_peaks) was used to identify peaks in the PXRD raw data for Catalyst 1.1, Catalyst Materials 1.1, Catalyst Material 1.2, Catalyst Material 2.2.1, Catalyst Material 2.4, and Catalyst Material 2.6 (Table 9, FIG. 14). This code identifies peaks by analyzing the prominence of maxima (prominence=150, wlen=100). Due to the setting used, very broad peaks overlapping with sharp peaks were not always identified by the code. Peak 9, located at approximately 22.2° 2θ, is the reference peak for relative intensities. VERSAL™ 250 Alumina has broad peaks at 13.91, 28.21, 38.46, 49.11, 55.66, 64.99° 2θ.

TABLE 9

| Peak # | Catalyst 1.1 | Catalyst Material 1.1 | Catalyst Material 1.2 | Catalyst Material 2.2.1 | Catalyst Material 2.4 | Catalyst Material 2.6 |
|---|---|---|---|---|---|---|
| | (2θ°) | | | | | |
| 1 | 6.67 | 6.63 | 6.65 | 6.67 | 6.65 | 6.65 |
| 2 | 7.88 | 7.84 | 7.86 | 7.88 | 7.86 | 7.88 |
| 3 | 9.02 | 9.00 | 9.02 | 9.02 | 9.00 | 9.05 |
| 4 | 10.85 | 10.81 | 10.85 | 10.85 | 10.85 | 10.87 |
| 5 | 13.05 | 13.03 | 13.05 | 13.07 | 13.05 | 13.12 |
| 6 | 13.36 | 13.34 | 13.36 | 13.38 | 13.38 | 13.47 |
| AlO(OH) 13.91 | — | — | — | — | — | — |
| 7 | 14.00 | 13.97 | 14.02 | 13.95 | 13.97 | 14.04 |
| 8 | 14.26 | 14.24 | 14.26 | 14.28 | — | — |
| 9 | 22.18 | 22.20 | 22.14 | 22.22 | 22.22 | 22.22 |
| 10 | 23.19 | 23.26 | 23.15 | 23.24 | — | 23.13 |
| 11 | 23.57 | 23.59 | 23.54 | 23.61 | 23.59 | 23.63 |
| 12 | 23.81 | 23.76 | 23.94 | 23.81 | 23.79 | — |
| 13 | 25.35 | 25.35 | 25.37 | 25.35 | 25.35 | 25.39 |
| 14 | 25.81 | 25.85 | 25.79 | 25.83 | — | — |
| 15 | 26.29 | 26.27 | 26.32 | 26.29 | 26.27 | 26.34 |
| 16 | 26.76 | 26.71 | 26.76 | 26.73 | 26.73 | 26.78 |
| 17 | 27.04 | 27.00 | 27.04 | 27.04 | — | — |
| 18 | 27.28 | 27.22 | 27.26 | 27.28 | 27.24 | 27.33 |
| 19 | 27.53 | 27.53 | 27.50 | 27.59 | — | 27.59 |
| 20 | 27.97 | — | 27.94 | 28.01 | — | — |
| AlO(OH) 28.21 | — | — | — | — | 28.21 | — |
| 21 | 28.23 | 28.21 | 28.23 | 28.23 | — | 28.25 |
| 22 | 28.78 | 28.78 | 28.78 | 28.76 | — | — |
| 23 | 29.29 | 29.26 | 29.31 | 29.29 | 29.24 | — |
| 24 | 29.86 | 29.86 | 29.88 | 29.86 | — | — |
| 25 | 30.54 | 30.56 | 30.58 | 30.52 | 30.61 | 30.54 |
| 26 | 31.40 | 31.40 | 31.44 | 31.38 | 31.38 | 31.44 |
| 27 | 31.90 | 31.88 | 31.93 | 31.88 | 31.86 | 31.93 |
| 28 | 32.78 | 32.76 | 32.76 | 32.76 | 32.85 | 32.63 |
| 29 | 34.10 | 34.02 | 34.08 | 34.04 | 34.17 | 33.97 |
| 30 | 34.68 | 34.68 | 34.63 | 34.72 | 34.59 | 34.65 |
| 31 | 35.01 | 34.98 | 35.01 | 35.03 | — | 35.01 |
| 32 | 35.42 | 35.40 | 35.42 | 35.45 | 35.42 | 35.49 |
| 33 | 36.19 | 36.17 | 36.19 | 36.24 | — | 35.49 |
| 34 | 37.03 | 37.03 | 37.05 | — | — | — |
| 35 | 37.49 | 37.49 | 37.54 | 37.58 | — | — |
| 36 | 38.15 | 38.09 | 38.13 | 38.17 | — | 38.24 |
| AlO(OH) 38.46 | — | — | — | — | 38.46 | — |
| 37 | 38.48 | 38.35 | 38.46 | 38.50 | — | 38.50 |
| 38 | 41.19 | 41.21 | 41.17 | 41.21 | 41.19 | 41.21 |
| 39 | 41.76 | 41.69 | 41.78 | 41.80 | — | 42.05 |
| 40 | 42.93 | 42.90 | 42.97 | 42.86 | 42.86 | 42.95 |
| 41 | 43.87 | 43.83 | 43.85 | 43.87 | 43.87 | 43.92 |
| 42 | 45.24 | 45.30 | 45.19 | 45.32 | 45.35 | 44.71 |
| 43 | 47.83 | 47.79 | 47.88 | 47.79 | — | — |
| 44 | 48.34 | 48.38 | 48.29 | 48.38 | — | — |
| 45 | 48.78 | 48.80 | 48.69 | 48.80 | — | — |
| AlO(OH) 49.11 | — | — | — | — | 49.33 | 49.44 |
| 46 | 51.40 | 51.33 | 51.44 | 51.35 | 51.31 | 51.40 |
| 47 | 51.95 | 51.84 | 51.99 | 51.99 | — | — |
| 48 | 52.56 | 52.56 | 52.63 | 52.56 | 52.50 | — |
| 49 | 53.60 | 53.66 | 53.57 | 53.64 | — | — |
| AlO(OH) 55.66 | — | — | — | — | — | — |
| 50 | 56.61 | 56.59 | 56.65 | 56.59 | 56.52 | 56.63 |
| 51 | 57.14 | 57.05 | 57.14 | 57.14 | 57.01 | 57.12 |
| 52 | 57.75 | 57.75 | 57.78 | 57.75 | 57.69 | 57.73 |
| 53 | 60.88 | 60.77 | 60.92 | 60.94 | 60.75 | 60.94 |
| 54 | 61.91 | 61.87 | 61.96 | 61.93 | 61.82 | 61.87 |
| AlO(OH) 64.99 | — | — | — | — | — | — |

Figure 15:
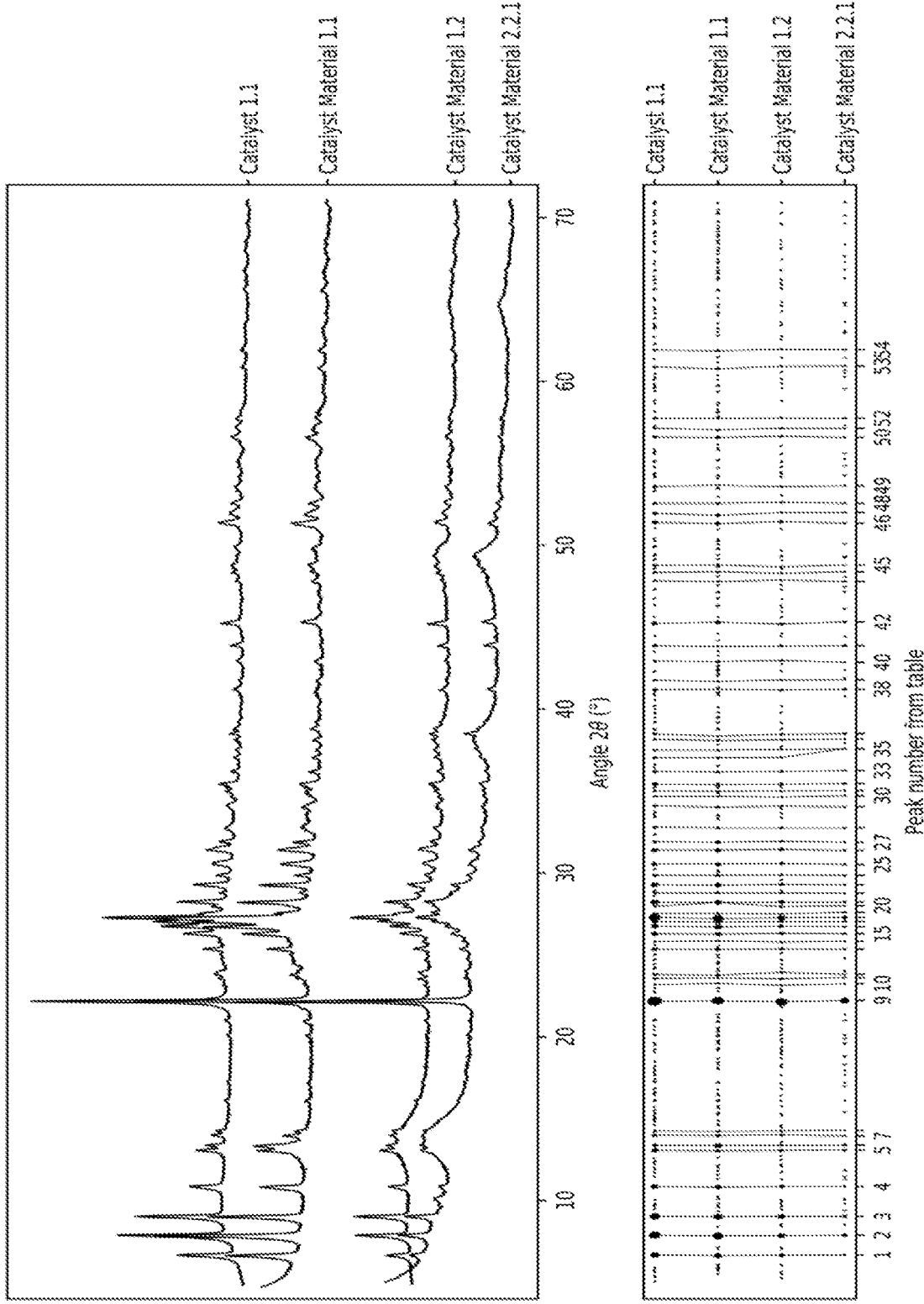
FIG. 15 shows overlaid PXRD diffractograms and related peak analysis for Catalyst 1.1, Catalyst Material 1.1, Catalyst Material 1.2, and Catalyst Material 2.2.1.

Catalyst Material 2.4 and Catalyst Material 2.6 have more VERSAL™ 250 Alumina in their formulations. The boehmite peaks from VERSAL™ 250 Alumina obscure keys peaks which the Python code could not resolve, as can be seen in Table 9. Therefore, the PXRD diffractograms for Catalyst Material 2.4 and Catalyst Material 2.6 were not included in the peak range and relative intensity analysis presented in Table 10 and FIG. 15 (peak range analysis for Catalyst 1.1, Catalyst Material 1.1, Catalyst Material 1.2, Catalyst Material 2.2.1). Peak 9, located at approximately 22.2° 2θ, is the reference peak for relative intensities. Since Catalyst Material 1.1 and Catalyst Material 2.2.1 contained less VERSAL™ 250 Alumina, almost all peaks could be resolved, with the exception of peak 20 for Catalyst Material 1.1 and peak 34 for Catalyst Material 2.2.1. These two specific data points are therefore omitted from the data ranges presented in Table 10.

TABLE 16

| Peak # | Min angle (2θ°) | Max angle | Min intensity (%) | Max intensity |
|---|---|---|---|---|
| 1 | 6.63 | 6.67 | 40.6 | 71.3 |
| 2 | 7.84 | 7.88 | 52.5 | 91.2 |
| 3 | 9.00 | 9.02 | 53.0 | 73.4 |
| 4 | 10.81 | 10.85 | 37.9 | 60.0 |
| 5 | 13.03 | 13.07 | 35.2 | 66.8 |
| 6 | 13.34 | 13.38 | 31.1 | 67.2 |
| 7 | 13.95 | 14.02 | 29.1 | 66.5 |
| 8 | 14.24 | 14.28 | 27.3 | 65.7 |
| 9 | 22.14 | 22.22 | 100.0 | 100.0 |
| 10 | 23.15 | 23.26 | 24.7 | 48.4 |
| 11 | 23.54 | 23.61 | 26.4 | 49.6 |
| 12 | 23.76 | 23.94 | 28.0 | 49.3 |
| 13 | 25.35 | 25.37 | 29.6 | 51.8 |
| 14 | 25.79 | 25.85 | 26.4 | 50.3 |
| 15 | 26.27 | 26.32 | 35.1 | 57.1 |
| 16 | 26.71 | 26.76 | 39.2 | 72.3 |
| 17 | 27.00 | 27.04 | 43.6 | 76.2 |
| 18 | 27.22 | 27.28 | 54.6 | 95.5 |
| 19 | 27.50 | 27.59 | 34.1 | 62.8 |
| 20* | 27.94 | 28.01 | 29.0 | 62.2 |
| 21 | 28.21 | 28.23 | 41.0 | 65.4 |
| 22 | 28.76 | 28.78 | 26.0 | 55.4 |
| 23 | 29.26 | 29.31 | 32.2 | 55.1 |
| 24 | 29.86 | 29.88 | 25.3 | 48.8 |
| 25 | 30.52 | 30.58 | 26.0 | 48.3 |
| 26 | 31.38 | 31.44 | 27.7 | 48.1 |
| 27 | 31.88 | 31.93 | 23.1 | 44.5 |
| 28 | 32.76 | 32.78 | 21.9 | 43.4 |
| 29 | 34.02 | 34.10 | 21.1 | 42.9 |
| 30 | 34.63 | 34.72 | 20.1 | 42.6 |
| 31 | 34.98 | 35.03 | 21.7 | 42.8 |
| 32 | 35.40 | 35.45 | 23.7 | 43.9 |
| 33 | 36.17 | 36.24 | 20.7 | 41.6 |
| 34† | 37.03 | 37.05 | 20.6 | 29.5 |
| 35 | 37.49 | 37.58 | 19.7 | 45.9 |
| 36 | 38.09 | 38.17 | 19.9 | 46.6 |
| 37 | 38.35 | 38.50 | 21.9 | 49.7 |
| 38 | 41.17 | 41.21 | 19.6 | 40.8 |
| 39 | 41.69 | 41.80 | 17.1 | 37.8 |
| 40 | 42.86 | 42.97 | 17.4 | 37.7 |
| 41 | 43.83 | 43.87 | 20.2 | 42.2 |
| 42 | 45.19 | 45.32 | 24.3 | 42.8 |
| 43 | 47.79 | 47.88 | 19.0 | 41.2 |
| 44 | 48.29 | 48.38 | 21.0 | 43.1 |
| 45 | 48.69 | 48.80 | 21.4 | 44.6 |
| 46 | 51.33 | 51.44 | 21.2 | 40.4 |
| 47 | 51.84 | 51.99 | 18.6 | 38.2 |
| 48 | 52.56 | 52.63 | 17.7 | 37.3 |
| 49 | 53.57 | 53.66 | 17.5 | 36.7 |
| 50 | 56.59 | 56.65 | 17.3 | 36.5 |
| 51 | 57.05 | 57.14 | 16.1 | 35.4 |
| 52 | 57.75 | 57.78 | 16.0 | 35.8 |
| 53 | 60.77 | 60.94 | 14.6 | 33.6 |
| 54 | 61.87 | 61.96 | 14.9 | 33.7 |

*Catalyst Material 1.1 omitted. Python code could not resolve overlapped peak.
†Catalyst Material 2.2.1 omitted. Python code could not resolve overlapped peak from boehmite alumina Weight Percent Analysis The bulk chemical weight percent, comparing the XRD phase fitting and the EDS measurements for Catalyst 1.1, Catalyst Materials 1.1, Catalyst Material 1.2, Catalyst Material 2.2.1, Catalyst Material 2.4, and Catalyst Material 2.6 are presented in Table 11.

TABLE 11

| Sample | Method | Element (wt. %) | | | | | |
|---|---|---|---|---|---|---|---|
| | | Mo | V | O | Be | Al | Ca |
| Catalyst 1.1 | EDS | 47.61 | 10.33 | 41.17 | — | 0.14 | — |
| | XRD | 53.22 | 13.07 | 33.71 | — | — | — |
| Catalyst Material 1.1 | EDS | 53.59 | 11.88 | 33.73 | * | 0.19 | — |
| | XRD | 53.28 | 11.39 | 33.81 | 1.52 | — | — |
| Catalyst Material 1.2 | EDS | 21.01 | 4.55 | 47.80 | * | 23.75 | — |
| | XRD | 18.76 | 4.61 | 47.45 | 1.68 | 27.13 | — |
| Catalyst Material 2.2.1 | EDS | 20.85 | 4.79 | 48.76 | * | 21.58 | 0.65 |
| | XRD | 15.44 | 3.84 | 48.93 | 1.59 | 29.07 | 0.86 |
| Catalyst Material 2.4 | EDS | 10.62 | 2.63 | 54.05 | * | 28.11 | — |
| | XRD | 5.22 | 2.38 | 51.99 | 0.59 | 39.82 | — |
| Catalyst Material 2.6 | EDS | 9.30 | 2.22 | 55.38 | * | 28.80 | — |
| | XRD | 6.30 | 2.02 | 51.63 | 0.66 | 39.13 | — |

* EDS is not well suited for identifying elements lighter than Na. As such, the contents of Be cannot be identified by this technique.

FTIR Analysis

Figure 13:
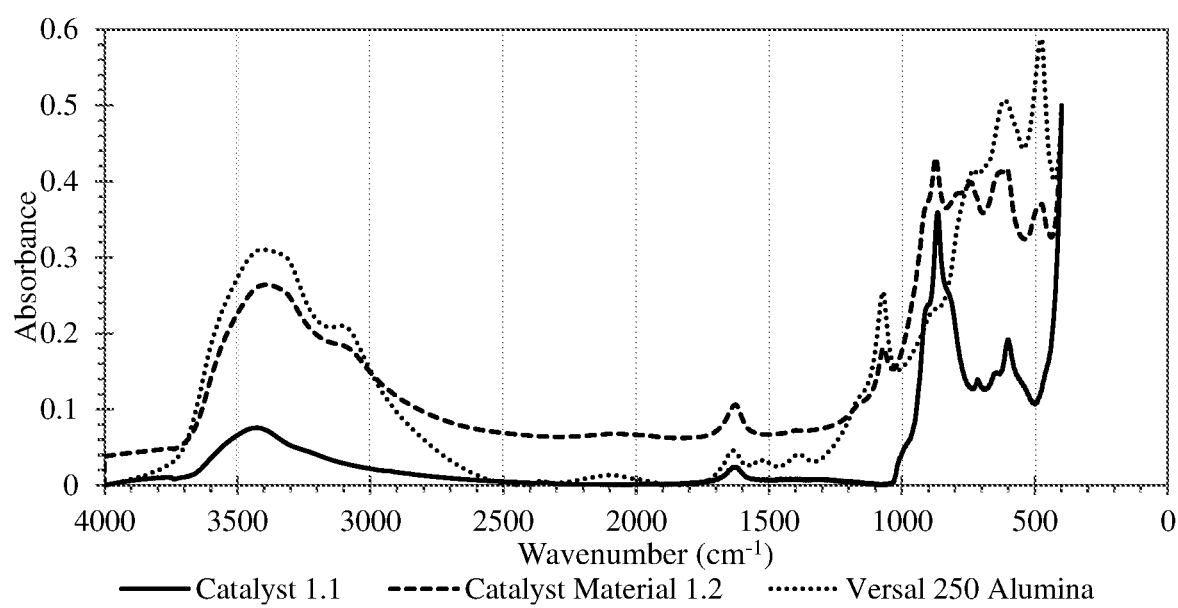
FIG. 13 shows FTIR plot overlays for Catalyst 1.1 compared to Catalyst Material 1.2.

The FTIR analysis for Catalyst 1.1 and Catalyst Materials 2.2 are presented in Table 12 as well as FIG. 13.

TABLE 12

| Sample | Peak Wavenumber (cm$^{-1}$) | Absorbance |
|---|---|---|
| Catalyst 1.1 | 3400 | 0.07 |
| | 1650 | 0.025 |
| | 870 | 0.34 |
| | 700 | 0.13 |
| | 600 | 0.19 |

TABLE 12-continued

| Sample | Peak Wavenumber (cm$^{-1}$) | Absorbance |
|---|---|---|
| Catalyst Material 1.2 | 3400 | 0.25 |
| | 3100 | 0.16 |
| | 1650 | 0.13 |
| | 870 | 0.42 |
| | 700 | 0.38 |
| | 600 | 0.40 |
| | 500 | 0.35 |

Crush Strength and Bulk Density

The crush strength of Catalyst Material 1.2 is presented in Table 13.

TABLE 13

| Sample | Press Speed (pellets/h) | Absolute Strength (N) | | | | | Radial Crush Strength (N/mm) |
|---|---|---|---|---|---|---|---|
| | | I | II | III | Average | Deviation | |
| Catalyst Material 1.2 | 2000 | 6.8 | 6.3 | 5.9 | 6.3 | 0.5 | 2.1 |
| | 2250 | 12.3 | 8.3 | 13.3 | 11.3 | 2.6 | 3.8 |
| | 2375 | 7.6 | 8.4 | 6.9 | 7.6 | 0.8 | 2.5 |
| Catalyst Material 2.2 | — | 7 | 13 | 7.7 | 9.2 | 3.3 | 3.1 |
| Catalyst Material 2.2.1 | — | 20.6 | 17.5 | 19.8 | 19.3 | 1.6 | 6.4 |
| Catalyst Material 2.3.1 | — | 11.7 | 9.4 | 7.7 | 9.6 | 2.0 | 3.2 |

Press speeds ranged from 1750 to 2500, even when not recorded. The radius of all pellets was measured to be 3 mm.

The bulk density for pelletized Catalyst Material 1.2 was measured to be 0.51 g/mL.

Synthesis of Samples
Sample Summary

TABLE 14

| Sample | Starting Material ratios (wt. %) | | | | Characterization |
|---|---|---|---|---|---|
| | Active Phase | BeO | VERSAL™ 250 Alumina | CaCO$_3$ | |
| Catalyst 1.1 | 100.00 | 0.00 | 0.00 | 0.00 | MRU, XRD, PSD, SEM, FTIR, ICP-MS |
| Catalyst Material 1.1 | 92.00 | 8.00 | 0.00 | 0.00 | MRU, XRD, PSD, SEM, ICP-MS |
| Catalyst Material 1.2 | 36.80 | 3.20 | 60.00 | 0.00 | MRU, XRD, PSD, SEM, BET, FTIR, TGA, ICP-MS, Pellet Strength |
| Catalyst 1.2 | 100.00 | 0.00 | 0.00 | 0.00 | MRU |
| Catalyst Material 2.1 | 36.80 | 3.20 | 60.00 | 0.00 | MRU |
| Catalyst Material 2.2 | 36.80 | 3.20 | 60.00 | 0.00 | Pellet Strength |
| Catalyst Material 2.2.1 | 36.06 | 3.14 | 58.80 | 2.00 | MRU, XRD, Pellet Strength |
| Catalyst Material 2.3 | 36.80 | 3.20 | 60.00 | 0.00 | — |
| Catalyst Material 2.3.1 | 33.86 | 2.94 | 55.20 | 8.00 | Pellet Strength |
| Catalyst Material 2.4 | 18.40 | 1.60 | 80.00 | 0.00 | MRU, XRD |
| Catalyst Material 2.5 | 18.40 | 1.60 | 80.00 | 0.00 | — |
| Catalyst Material 2.5.1 | 18.03 | 1.57 | 78.40 | 2.00 | MRU |
| Catalyst Material 2.6 | 18.40 | 1.60 | 80.00 | 0.00 | MRU, XRD |

TABLE 14-continued

| | Starting Material ratios (wt. %) | | | | |
|---|---|---|---|---|---|
| Sample | Active Phase | BeO | VERSAL™ 250 Alumina | CaCO$_3$ | Characterization |
| Catalyst 1.3 | 100.00 | 0.00 | 0.00 | 0.00 | MRU |
| Catalyst Material 3.1 | 92.00 | 8.00 | 0.00 | 0.00 | MRU |
| Catalyst Material 3.1.1 | 36.80 | 3.20 | 60.00 | 0.00 | MRU |
| Catalyst Material 3.2 | 64.40 | 5.60 | 30.00 | 0.00 | — |
| Catalyst Material 3.2.1 | 36.80 | 3.20 | 30.00 | 30.00 | MRU |
| Catalyst Material 3.2.2 | 36.80 | 3.20 | 30.00 | 30.00 | MRU |
| Catalyst Material 3.3.1 | 36.80 | 3.20 | 0.00 | 60.00 | MRU |
| Catalyst Material 3.3.2 | 36.80 | 3.20 | 0.00 | 60.00 | MRU |
| Catalyst Material 3.4.1 | 26.31 | 2.29 | 0.00 | 71.40 | MRU |
| Catalyst Material 3.4.2 | 26.31 | 2.29 | 0.00 | 71.40 | - |
| Catalyst 1.4 | 100.00 | 0.00 | 0.00 | 0.00 | MRU |
| Catalyst Material 4.1 | 18.40 | 1.60 | 80.00 | 0.00 | MRU |
| Catalyst Material 4.1.1 | 17.48 | 1.52 | 76.00 | 5.00 | MRU |

Synthesis of Catalyst 1.1

A solution of $(NH_4)_6Mo_7O_{24} \cdot 4H_2O$ (44.20 g, 35.77 mmol, white solid) in 600 mL of dH$_2$O was prepared in a 2-L RBF equipped with magnetic stir bar. A solution of VOSO$_4$.3.46H$_2$O (14.07 g, 62.95 mmol, bright blue solid) in 600 mL of dH$_2$O was prepared in a 1-L beaker equipped with magnetic stir bar. Both solutions were stirred in a 60° C. water bath until homogeneous. The blue vanadium solution was then added to the clear colorless molybdenum solution. This resulted in a dark purple solution with a fine suspension. Sodium dodecyl sulfate (SDS) (13.57 g, 47.06 mmol, white solid) was added to the reaction mixture. The purple slurry was left to stir at 60° C. for 30 minutes.

The reaction mixture was transferred to a glass liner, with a total volume of about 1375 mL measured after rinsing. The liner was loaded into a 2-L Parr reactor and the gap filled with dH$_2$O. The reactor was sealed and the head space evacuated and backfilled with N$_2$ gas 10× times. The headspace was left under 15 psig N$_2$ gas and sealed. A heating mantel and insulation was used to heat the reaction for 24 hours at 230° C. (heating mantel controller set to 240° C.). Once cooled to room temperature, the reactor was vented, and the contents filtered using a Buchner funnel and 4 quantitative filter papers. The filter cake was rinsed with 1180 mL of room temperature dH$_2$O and 900 mL of 80° C. dH$_2$O. The filtrate was a dark blue color and the product was a silvery/grey purple color.

The filter cake was dried in the oven at 90° C. overnight with 42.42 g of product being recovered. The dry powder product was roughly crushed using a spatula, and then loaded into the muffle furnace for an air treatment (26 hours at 280° C.). There was 20.92 g of product recovered after the air treatment. The dry powder product was loaded into two quartz boats and centered in the quartz tube of the QRU. The quartz tube was purged with purified nitrogen overnight. The furnace was then ramped up to 400° C. at a rate of 1.6° C./min. The catalyst was calcined at 400° C. for 2 hours and then cooled to ambient temperature naturally.

Synthesis of Catalyst Material 1.1

To a 400 mL beaker was charged 18.3035 g of Catalyst 1.1 and 1.5949 g of beryllium oxide with 75 mL of distilled water forming a purple slurry. The beaker was clamped in an oil bath and an overhead agitator assembly was set up using a one-inch TEFLON™ stir blade and a glass stir shaft. The overhead agitator assembly was set to 100 rpm and the oil bath was set to 100° C. The purple slurry was stirred and heated for 1.16 hours until the slurry became a black/purple paste. The beaker containing the paste was removed from the oil bath. The oil on the outside of the beaker was removed using heptane and the beaker was placed in a 90° C. oven to dry for 18 hours. After such time, the beaker containing the dried black/purple paste was transferred to a muffle furnace where it was calcined for 2 hours with a 30-minute ramp time. Subsequently, the beaker containing the black/purple powder was removed from the muffle furnace yielding 19.0480 g of dark purple powder.

Synthesis of Catalyst Material 1.2

To a 400 mL beaker was charged 16.0480 g of Catalyst Material 1.1 and 24.0858 g of VERSAL™ 250 Alumina along with 75 mL of distilled water forming a dark purple slurry. The beaker was clamped in an oil bath and an overhead agitator was assembled using a one-inch TEFLON™ stir blade and a glass stir shaft. The overhead agitator was set to 100 rpm and the oil bath was set to 100° C. The dark purple slurry was heated for 55 minutes until the slurry became a dark purple paste. The oil on the outside of the beaker containing the dark purple paste was removed using heptane and the beaker and paste were dried in a 90° C. oven for 18 hours. Following the drying step at 90° C. the dried paste in the beaker was removed, the powder was ground using a mortar and pestle and muffle furnace calcined at 350° C. for 2 hours with a ramp time of 30 minutes.

The catalyst was pelletized using the auto press and the crush strength measurements were taken at three different speeds. Crush strength was determined using ASTM D4179.

The bulk density was also measured for this catalyst using a standard bulk density measurement procedure.

Synthesis of Catalyst 1.2

Three separate vessels were filled with distilled water and heated to the desired temperature. The starting materials were dissolved in each vessel while stirring. Table 15 shows the conditions of the starting chemicals preparation:

TABLE 15

| Vessel ID | Volume of dH$_2$O (L) | Heat to (° C.) | Chemicals Added | Mass of Chemical (g) | dH$_2$O Rinse After Dry Chemical Transfer into Vessel | H$_2$O Rinse After Solution Transfer to Reactor |
|---|---|---|---|---|---|---|
| Vessel-1 | 19 | 60 | Vanadyl sulphate hydrate | 664 | 1 | 2 |
| Vessel-2 | 10 | 48 | sodium dodecyl sulfate pellets | 644 | 1 | 2 |
| Vessel-3 | 19 | 30 | ammonium molybdate tetrahydrate | 2104 | 1 | 2 |

The solutions were each stirred for about 10 minutes until homogeneous solution were obtained. The total water used for the reaction, including rinsing the vessels, was 57 L. The solution of ammonium molybdate tetrahydrate from Vessel-1 was pumped into the 100-L reactor vessel at the pump rate of 3.2 L/min. Once transferred, the reactor was stirred and the solution of vanadyl sulfate hydrate from Vessel-2 was added to the 100-L reactor vessel at the pump rate of 3.2 L/min. Lastly, the sodium dodecyl sulfate solution in Vessel-3 was pumped into the 100-L reactor vessel at the rate of 3.2 L/min. The reaction mixture was allowed to stir in the reactor for 30 minutes. While the reaction was stirring, the headspace of the reactor was purged with N$_2$ to displace all the air present. Upon hitting the 30-minute mark, the reactor was sealed, and the reactor heaters were set to 230° C. After having reached an internal temperature of 220° C. and pressure of 390 psig, the hydrothermal reaction was allowed to proceed for 24 hours. The reactor was then cooled to 50° C. and vented. The contents of the reactor were filtered, and the filtrate was rinsed with 140 L of distilled water. The wet catalyst cake was dried in an oven at 90° C. for 48 hours.

The catalyst was loaded in a tube furnace and heated at 285° C. for 26 hours under a low flow of air (500 sccm). After the air treatment, the catalyst was calcined at 400° C. for 3 hours under a flow of N$_2$ (800-1000 sccm) in the same tube furnace. After the N$_2$ calcination, the catalyst was treated a second time at 350° C. for 3 hours in air.

Synthesis of Catalyst Material 2.1

To a 100 mL beaker was charged 2.3684 g of Catalyst 1.2, 12.0920 g of VERSAL™ 250 Alumina, 0.6472 g of beryllium oxide and 33 mL of distilled water. The beaker was clamped into an oil bath and an overhead agitator was set up with a glass stir rod and a 0.5-inch TEFLON™ stir blade. The aqueous mixture was stirred for 3 hours and 15 minutes in a 100° C. oil bath with the overhead agitator stirring at 100 rpm. The resulting paste was dried at 90° C. for 18 hours. Subsequently, the dried powder was then muffle furnace treated at 350° C. for 2 hours with a ramp time of 30 minutes yielding 18.2475 g of final catalyst material.

Synthesis of Catalyst Material 2.2

To a 400-mL beaker was charged 25.7860 g of Catalyst 1.2, 42.0149 g of VERSAL™ —250 Alumina, 2.2420 g of Beryllium Oxide and 150 mL of distilled water. These additions formed a light purple aqueous mixture. The beaker was clamped into an oil bath and an overhead agitator was assembled using a ½" TEFLON™ stir blade and a glass stir shaft. The oil bath was heated to 100° C. and the overhead agitator was set to 99 rpm. The aqueous mixture was heated and stirred for 5 hours and 30 minutes forming a light purple paste. The paste was dried in an oven at 90° C. for 18 hours forming a light purple powder. The light purple powder was transferred into two smaller beakers. The catalyst powder in these beakers were muffle furnace calcined at 350° C. for 2 hours with a ramp time of 30 minutes yielding 59.36 g. A portion of Catalyst Material 2.2 was pressed.

Synthesis of Catalyst Material 2.2.1

To a 250 mL beaker was charged 20.0837 g of Catalyst Material 2.2, 0.4016 g of calcium carbonate and 40 mL of distilled water forming a black/purple aqueous mixture. The beaker was clamped into an oil bath, the oil bath was heated to 100° C. An overhead agitator assembly was assembled using a glass stir rod and a 0.5-inch TEFLON™ stir blade. The slurry was stirred and heated at 100° C. for 1 hour. The resulting paste was dried in an oven for 18 hours. The resulting powder was further dried at 200° C. for 2 hours. The resulting powder was pelletized on the auto-press forming 9.61 g of pellets and 8.51 g of powder.

Synthesis of Catalyst Material 2.3

Catalyst 1.2 in the amount of 27.6320 g was charged a 600 ml beaker, followed by addition of 92.5221 g of VERSAL™ 250 Alumina, 2.4056 g of beryllium oxide and 250 ml of distilled water. The beaker was clamped into an oil bath and an overhead agitator was assembled using a glass stir rod and a 0.5-inch TEFLON™ stir blade. The oil bath was heated to 100° C. and the overhead agitator was set to 100 rpm. The mixture was left to stir for 2 hours and 20 minutes, after which it became a purple-black paste. The beaker containing the paste was heated in a 90° C. oven for about 18 hours (overnight drying). Subsequently, the dried paste was calcined in a muffle furnace at 350° C. for two hours with a 30-minute ramp time in air atmosphere with convective air exchange.

Synthesis of Catalyst Material 2.3.1

To a 250 mL beaker was charged 1.6984 g of calcium carbonate and 18.374 g of Catalyst Material 2.3. To the beaker was charged 57 mL of distilled water. The Catalyst Material 3.1 and calcium carbonate mixture was bubbled and the solution turned a yellow/green color. The beaker was clamped into an oil bath and an overhead agitator was assembled using a glass stir rod and a 0.5-inch TEFLON™ stir blade. The oil bath was heated to 100° C. and the overhead agitator was set to 100 rpm. The mixture was left to stir for 2 hours, after which it became a grey purple paste. The beaker containing the paste was heated in a 90° C. oven for 18 hours. Subsequently, the dried paste was ground, and muffle furnace calcined at 350° C. for two hours with a 30-minute ramp time. The resulting grey powder yielding 15.2 g was ground and sieved to 500 μm and pelletized using an auto-press.

Synthesis of Catalyst Material 2.4

To a 250-mL beaker was charged 10.0263 g of Catalyst 1.2, 0.8056 g of beryllium oxide, 43.2188 g of VERSAL™ 250 Alumina, and 150 mL of distilled water. The beaker was clamped in a 100° C. oil bath and an overhead agitator assembly was setup with a 0.5-inch TEFLON™ stir blade and a glass stir rod. The agitator speed was set to 100 rpm and the suspension was allowed to stir for 3 hours to form a thick paste. The mixture was removed from the oil bath and dried in an oven at 90° C. over the weekend. The beaker was then placed in a muffle furnace and calcined at 350° C. for 2 hours, with a 30-minute ramp time.

Synthesis of Catalyst Material 2.5

To a 250-mL beaker was charged 10.0807 g of Catalyst 1.2. 0.8097 g, of beryllium oxide, 42.2380 g of VERSAL™ 250 Alumina and 150 mL of distilled water. The beaker was clamped into an oil bath and an overhead agitator was assembled using a 0.5-inch TEFLON™ stir blade and a glass stir shaft. The oil bath was heated to 100° C. and the overhead agitator was set to 100 rpm. The purple/grey aqueous mixture was heated and stirred for 3 hours. The resulting grey/purple paste was dried in a 90° C. oven for 18 hours. Subsequently, the dried light purple powder was calcined in a muffle furnace at 350° C. for 2 hours with a 30-minute ramp time yielding 48.6073 g of light purple powder.

Synthesis of Catalyst Material 2.5.1

To Catalyst Material 2.5 was charged 0.9920 g of $CaCO_3$ and 153 mL of distilled water. The beaker was clamped into an oil bath and an overhead agitator was assembled using a 0.5-inch TEFLON™ stir blade and glass stir shaft. The oil bath was heated to 100° C. and the overhead agitator was set to 98 rpm. The aqueous mixture was heated and stirred for 5 hours and 30 minutes forming a paste. The light purple paste was dried in a 90° C. oven for 18 hours yielding 45.5219 g of light purple powder. This material was then treated at 380° C.

Synthesis of Catalyst Material 2.6

To a 50-mL beaker was charged 2.0543 g of Catalyst 1.2, 0.1602 g of beryllium oxide, 8.6317 g of VERSAL™ 250 Alumina and 20 mL of distilled water. The contents were manually mixed to form a uniform paste. The beaker was placed in an oven at 90° C. overnight. The beaker was then transferred to a muffle furnace and calcined at 350° C. for 2 hours with a 30 minute ramp time. The resulting purple catalyst material powder was ground and yielded 9.0129 g.

Synthesis of Catalyst 1.3

Three separate vessels were filled with distilled water and heated to the desired temperature. The starting materials were dissolved in each vessel while stirring. Table 16 shows the conditions of the starting chemicals preparation:

TABLE 16

| Vessel ID | Volume of $dH_2O$ (L) | Heat to (° C.) | Chemicals Added | Mass of Chemical (g) | $dH_2O$ Rinse After Dry Chemical Transfer into Vessel | $H_2O$ Rinse After Solution Transfer to Reactor |
|---|---|---|---|---|---|---|
| Vessel-1 | 19 | 60 | Vanadyl sulphate hydrate | 664 | 1 | 2 |
| Vessel-2 | 10 | 48 | sodium dodecyl sulfate pellets | 644 | 1 | 2 |
| Vessel-3 | 19 | 30 | ammonium molybdate tetrahydrate | 2104 | 1 | 2 |

The solutions were each stirred for about 10 minutes until homogeneous solution were obtained. The total water used for the reaction, including rinsing the vessels, was 57 L. The solution of ammonium molybdate tetrahydrate from Vessel-1 was pumped into the 100-L reactor vessel at the pump rate of 3.2 L/min. Once transferred, the reactor was stirred and the solution of vanadyl sulfate hydrate from Vessel-2 was added to the 100-L reactor vessel at the pump rate of 3.2 L/min. Lastly, the sodium dodecyl sulfate solution in Vessel-3 was pumped into the 100-L reactor vessel at the rate of 3.2 L/min. The reaction mixture was allowed to stir in the reactor for 30 minutes. While the reaction was stirring, the headspace of the reactor was purged with $N_2$ to displace all the air present. Upon hitting the 30-minute mark, the reactor was sealed, and the reactor heaters were set to 230° C. After having reached an internal temperature of 220° C. and pressure of 390 psig, the hydrothermal reaction was allowed to proceed for 24 hours. The reactor was then cooled to 50° C. and vented. The contents of the reactor were filtered, and the filtrate was rinsed with 140 L of distilled water. The wet catalyst cake was dried in an oven at 90° C. for 48 hours.

The catalyst was loaded in a tube furnace and heated at 285° C. for 26 hours under a low flow of air (500 sccm). After the air treatment, the catalyst was calcined at 400° C. for 3 hours under a flow of $N_2$ (800-1000 sccm) in the same tube furnace. After the $N_2$ calcination, the catalyst was treated a second time at 350° C. for 3 hours in air.

Synthesis of Catalyst Material 3.1

To a 400-mL beaker was loaded 49.97 g of Catalyst 1.3 and 4.35 g of beryllium oxide. The mixture was stirred manually with a stir stick and then about 120 mL of $dH_2O$ was added. The beaker was placed in an oil bath at 100° C. and stirred at 100 rpm with an overhead stirrer. After about 2 hours, the mixture had formed a thick paste. The beaker was transferred to an oven at 90° C. and left overnight, yielding 56.99 g of catalyst material powder. The beaker was then placed in a muffle furnace at 350° C. for 2 hours (in addition to a 30-minute ramp to 350° C.) and left to cool overnight. The calcined catalyst was dark purplish-grey powder color and 54.53 g of material was recovered. The powder was submitted to MRU for testing.

Synthesis of Catalyst Material 3.1.1

To a 100-mL beaker was loaded 4.00 g of Catalyst Material 3.1 (dark purplish-grey powder) and 6.00 g of VERSAL™ 250 (white powder). The mixture was stirred manually with a stir stick and then about 34 mL of dH$_2$O was added. The beaker was placed in an oil bath at 100° C. and stirred at 100 rpm with an overhead stirrer. After about 1 hour, the mixture had formed a thick paste. The beaker was transferred to an oven at 90° C. and left overnight, yielding 10.16 g of catalyst material powder. The beaker was then placed in a muffle furnace at 350° C. for 2 hours with a 30-minute ramp time and left to cool overnight, yielding 9.85 g of light grey catalyst material powder. The calcined material was ground using a mortar and pestle. The powder was submitted to MRU for testing.

Synthesis of Catalyst Material 3.2

To a 100-mL beaker was loaded 8.00 g of baseline material Catalyst Material 3.1 (dark purplish-grey powder) and 6.00 g of VERSAL™ 250 alumina (white powder). The mixture was stirred manually with a stir stick and then about 31 mL of dH$_2$O was added. The beaker was placed in an oil bath at 100° C. and stirred at 100 rpm with an overhead stirrer. After about 1 hour, the mixture had formed a thick paste. The beaker was transferred to an oven at 90° C. and left overnight, yielding 13.32 g of light grey powder. The powder was placed in a muffle furnace at 350° C. for 2 hours (in addition to a 30-minute ramp to 350° C.) and left to cool overnight. This yielded 13.08 g of light grey material which was roughly crushed with a spatula.

Synthesis of Catalyst Material 3.2.1

To the 100-mL beaker containing Catalyst Material 3.2 was loaded 5.61 g of calcium carbonate and 32.3 mL of distilled water and manually stirred with a stir stick. The beaker was placed in an oil bath at 100° C. and stirred at 100 rpm with an overhead stirrer. After about 1 hour, the mixture had formed a thick paste. The beaker was transferred to an oven at 90° C. and left overnight, yielding 16.53 g of grey/beige catalyst material. The material was ground using a mortar and pestle. The powder was submitted for MRU testing.

Synthesis of Catalyst Material 3.2.2

To a 100 mL beaker was charged 8.04 g of Catalyst Material 3.2.1. This beaker was then placed in a muffle furnace and calcined at 350° C. for 2 hours with a 30 minute ramp time and left to cool overnight. This yielded beige powder. The powder was submitted to MRU for testing.

Synthesis of Catalyst Material 3.3.1

To a 250-mL beaker was loaded 8.00 g of Catalyst Material 3.1, dark purplish-grey powder), 12.00 g of calcium carbonate (white powder). The mixture was stirred manually with a stir stick and then about 75 mL of dH$_2$O was added. The beaker was placed in an oil bath at 100° C. and stirred at 100 rpm with an overhead stirrer. After about 2 hours, the mixture had formed a thick paste. The beaker was transferred to an oven at 90° C. and left overnight, yielding 18.25 g of catalyst material powder. The powder (grey/beige) was ground using a mortar and pestle. The powder was submitted to MRU for testing.

Synthesis of Catalyst Material 3.3.2

To another 100 mL beaker was charged 9.22 g of Catalyst Material 3.3.1, was then placed in a Lindberg Blue M programmable muffle furnace at 350° C. for 2 hours (in addition to a 30-minute ramp to 350° C.) and left to cool overnight. This yielded 8.92 g of beige powder. The powder was submitted to MRU for testing.

Synthesis of Catalyst Material 3.4.1

To a 100-mL beaker was loaded 8.00 g of Catalyst Material 3.1 (dark purplish-grey powder) and 20.01 g of calcium carbonate (white powder). The mixture was stirred manually with a stir stick and then about 71 mL of dH$_2$O was added. The beaker was placed in an oil bath at 100° C. and stirred at 100 rpm with an overhead stirrer. After about 1 hour, the mixture had formed a thick paste. The beaker was transferred to an oven at 90° C. and left overnight, yielding 25.72 g of grey/beige catalyst material. The powder was ground using a mortar and pestle. The powder was submitted to MRU for testing.

Synthesis of Catalyst Material 3.4.2

The remaining powder was placed in a muffle furnace at 350° C. for 2 hours with a 30-minute ramp time and left to cool overnight. This yielded 13.14 g of beige material.

Synthesis of Catalyst 1.4

Catalyst 1.2 and Catalyst 1.3 were combined.

Synthesis of Catalyst Material 4.1

In a Pyrex dish was mixed 325.00 g of Catalyst 1.2, 28.2641 g of beryllium oxide, 1413.0 g of VERSAL™ 250 alumina and 3600 mL of dH$_2$O. The mixture was manually mixed with large stainless-steel serving utensils. In a second large glass Pyrex dish was mixed 325.00 g of catalyst active phase, 28.2600 g of BeO, 1413.0 g of VERSAL™ 250 alumina and 3600 mL of dH$_2$O. The mixture was manually mixed, and then transferred into the larger Pyrex dish. The combined mixture was further manually mixed, until it appeared to be homogeneous (approximately 20 minutes of mixing). It was noted that the paste was a little wet, and that 250 mL less could be used for the next batch. The large Pyrex dish was loaded into the oven at 90° C. overnight. The resulting powder was transferred into 3-L beakers (two beakers at time) and loaded into a Lindberg Blue M programmable muffle furnace and calcined at 350° C. for 2 hours (in addition to a 30-minute ramp to 350° C.), before being left to cool overnight. The powder was then ground using a RETSCH® BB50 jaw crusher.

In a Pyrex dish was mixed 324.872 g of catalyst active phase Catalyst 1.4, 28.262 g of BeO, 1413.0 g of VERSAL™ 250 alumina and 3500 mL of dH$_2$O. The mixture was manually mixed with large stainless-steel serving utensils. In a second large glass Pyrex dish was mixed 325.075 g of catalyst active phase, 28.262 g of BeO, 1408.0 g of VERSAL™ 250 alumina and 3500 mL of dH$_2$O. The mixture was manually mixed, and then transferred into the larger Pyrex dish. The combined mixture was further manually mixed, until it appeared to be homogeneous (approximately 20 minutes of mixing). The large Pyrex dish was loaded into the oven at 90° C. overnight. The resulting powder was transferred into 3-L beakers (two beakers at time) and loaded into a Lindberg Blue M programmable muffle furnace and calcined at 350° C. for 2 hours (in addition to a 30-minute ramp to 350° C.), before being left to cool overnight. The powder was then ground using a RETSCH® BB50 jaw crusher.

In a Pyrex dish was mixed 324.998 g of catalyst active phase Catalyst 1.3, 28.2638 g of BeO, VERSAL™ 250 alumina (mass was not recorded, but assumed to be 1413.0) and 3500 mL of dH$_2$O. The mixture was manually mixed with large stainless-steel serving utensils. In a second large glass Pyrex dish was mixed 298.117 g of catalyst active phase, 25.9232 g of BeO, 1296.0 g of VERSAL™ 250 alumina and 3500 mL of dH$_2$O. The mixture was manually mixed, and then transferred into the larger Pyrex dish. The combined mixture was further manually mixed, until it appeared to be homogeneous (approximately 20 minutes of mixing). It was noted that the paste was a little wet, and that 250 mL less could be used for the next batch. The large Pyrex dish was loaded into the oven at 90° C. overnight. The resulting powder was transferred into 3-L beakers and loaded into a Lindberg Blue M programmable muffle furnace and calcined at 350° C. for 2 hours (in addition to a 30-minute ramp to 350° C.), before being left to cool overnight. The powder was then ground using a RETSCH® BB50 jaw crusher.

All catalyst materials from these three batches were combined to for Catalyst Material 4.1.

Synthesis of Catalyst Material 4.1.1

FeMo Cat Ltd. received 10 607 g of Catalyst Material 4.1. To this was added 530 g of calcium carbonate via dry mixing. A total 11 137 g of catalyst material was fed into the RTP 41 press, with 9 898 g of pellets being recovered. Of the 1 239 g lost, there was 185 g of recoverable run material and 550 g of dust; other losses totaled 504 g. The tableting yield was therefore 88.9%, though the process potential yield was 95.4%. Calcination in an air atmosphere of the resulting catalyst material pellets led to a 14.6 wt. % mass loss, and thus the final pellet mass was 8 456 g. The calcination furnace was ramped to 200° C. over 2 hours and dwelled at 200° C. for 2 hours. It was then further ramped to 350° C. over 2 hours and dwelled at 350° C. for 2 hours, before cooling back down to 50° C. over 2 hours.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

INDUSTRIAL APPLICABILITY

Catalyst materials for the oxidative dehydrogenation of alkanes such as ethane.

The invention claimed is:

1. A catalyst material, comprising:
molybdenum;
vanadium;
beryllium; and
oxygen,
wherein:
 a molar ratio of molybdenum to vanadium is from 1:0.25 to 1:0.65;
 a molar ratio of molybdenum to beryllium is from 1:0.25 to 1:0.85; and
 oxygen is present at least in an amount to satisfy the valency of any present metal oxides, wherein the catalyst material has a 35% conversion temperature of ethane in a gas stream being converted to a product other than ethane at a weight hourly space velocity (WHSV) of 2.90 h$^{-1}$, a gas hourly space velocity (GHSV) of 2000 to 3000 h$^{-1}$, an inlet pressure in a range of 1 pound per square inch gauge (psig) to 2.5 psig, and an outlet pressure in a range of 0 psig to 0.5 psig of from about 300° C. to about 400° C.; and wherein the catalyst material has a selectivity to ethylene of from about 65% to 99% in the oxidative dehydrogenation of ethane at the 35% conversion temperature.

2. The catalyst material of claim 1, wherein the molar ratio of molybdenum to vanadium is from 1:0.35 to 1:0.55.

3. The catalyst material of claim 1, wherein the molar ratio of molybdenum to beryllium is from 1:0.35 to 1:0.75.

4. The catalyst material of claim 1, wherein the catalyst material has an amorphous phase of from 45 wt. % to 75 wt. %.

5. The catalyst material of claim 1, wherein the catalyst material has an average crystallite size of greater than 50 nm.

6. The catalyst material of claim 1, wherein the catalyst material has a mean particle size from 0.5 μm to 10 μm.

7. The catalyst material of claim 1, wherein the catalyst material has at least one XRD diffraction peak (2θ degrees) selected from the group consisting of 6.5±0.2, 7.8±0.2, 8.9±0.2, 10.8±0.2, 13.2±0.2, 14.0±0.2, 22.1±0.2, 23.8±0.2, 25.2±0.2, 26.3±0.2, 26.6±0.2, 27.2±0.2, 27.6±0.2, 28.2±0.2, 29.2±0.2, 30.5±0.2, and 31.4±0.2, and wherein the XRD is obtained using CuKα radiation.

8. The catalyst material of claim 1, wherein the catalyst material is an oxidative dehydrogenation catalyst material.

9. A catalyst material, comprising:
molybdenum;
vanadium;
beryllium;
aluminum; and
oxygen,
wherein:
 a molar ratio of molybdenum to vanadium is from 1:0.25 to 1:0.65;
 a molar ratio of molybdenum to beryllium is from 1:0.25 to 1:1.7;
 a molar ratio of molybdenum to aluminum is from 1:1 to 1:9; and
 oxygen is present at least in an amount to satisfy the valency of any present metal oxides, wherein the catalyst material has a 35% conversion temperature of ethane in a gas stream being converted to a product other than ethane at a weight hourly space velocity (WHSV) of 2.90 h$^{-1}$, a gas hourly space velocity (GHSV) of 2000 to 3000 h$^{-1}$, an inlet pressure in a range of 1 pound per square inch gauge (psig) to 2.5 psig, and an outlet pressure in a range of 0 psig to 0.5 psig of from about 300° C. to about 400° C.; and wherein the catalyst material has a selectivity to ethylene of from about 65% to 99% in the oxidative dehydrogenation of ethane at the 35% conversion temperature.

10. The catalyst material of claim 9, wherein the molar ratio of molybdenum to vanadium is from 1:0.35 to 1:0.55.

11. The catalyst material of claim 9, wherein the molar ratio of molybdenum to beryllium is from 1:0.35 to 1:0.75.

12. The catalyst material of claim 9, wherein the molar ratio of molybdenum to aluminum is from 1:2 to 1:8.

13. The catalyst material of claim 9, wherein at least a portion of the aluminum in the catalyst material is present as an aluminum oxide.

14. The catalyst material of claim 9, wherein at least a portion of the aluminum in the catalyst material is present as gamma alumina.

15. The catalyst material of claim 9, wherein the catalyst material has an amorphous phase of from 50 wt. % to 80 wt. %.

16. The catalyst material of claim 9, wherein the catalyst material is an oxidative dehydrogenation catalyst material.

* * * * *